United States Patent
Tam et al.

(10) Patent No.: US 8,207,217 B2
(45) Date of Patent: Jun. 26, 2012

(54) CRYSTALLINE FORMS OF THE MONO-SODIUM SALT OF D-ISOGLUTAMYL-D-TRYPTOPHAN

(75) Inventors: Tim Fat Tam, Vaughan (CA); Blaise N'Zemba, Brampton (CA); Regis Leung-Toung, Mississuaga (CA); Yingsheng Wang, Toronto (CA); Yanqing Zhao, Toronto (CA); Lily Yu, Woodbridge (CA)

(73) Assignee: Apotex Technologies Inc, Toronto, Ontario (CA)

( * ) Notice: Subject to any disclaimer, the term of this patent is extended or adjusted under 35 U.S.C. 154(b) by 391 days.

(21) Appl. No.: 12/527,289

(22) PCT Filed: Feb. 11, 2008

(86) PCT No.: PCT/CA2008/000271
§ 371 (c)(1),
(2), (4) Date: Aug. 14, 2009

(87) PCT Pub. No.: WO2008/098355
PCT Pub. Date: Aug. 21, 2008

(65) Prior Publication Data
US 2010/0029742 A1 Feb. 4, 2010

(30) Foreign Application Priority Data

Feb. 16, 2007 (CA) .................................. 2579119

(51) Int. Cl.
*A61K 31/404* (2006.01)
*C07D 209/12* (2006.01)
(52) U.S. Cl. ........................................ 514/419; 548/495
(58) Field of Classification Search .................. 548/495
See application file for complete search history.

(56) References Cited

OTHER PUBLICATIONS

RN 863988-88-9 retrieved from CAS Registry, entered in STN on Sep. 27, 2005.*

* cited by examiner

*Primary Examiner* — Shawquia Young

(57) ABSTRACT

The present invention relates to crystalline forms of the mono-sodium salt of D-isoglutamyl-D-tryptophan, pharmaceutical compositions comprising them, their use in the treatment of various diseases and conditions, and processes for their preparation. In particular, the present invention relates the crystal modification 1 (polymorphic form F), the crystal modification 2 (polymorphic form I), and the crystal modification 3 (polymorphic form X) of the mono-sodium salt of D-isoglutamyl-D-tryptophan.

9 Claims, 9 Drawing Sheets

CRYSTALLINE FORMS OF THE MONO-SODIUM SALT OF D-ISOGLUTAMYL-D-TRYPTOPHAN

FIELD OF THE INVENTION

The present invention relates to crystalline forms of the mono-sodium salt of D-isoglutamyl-D-tryptophan, processes for their preparation, pharmaceutical preparations comprising them, and their use in the treatment of various conditions and diseases. In particular, the present invention relates to crystal modification 1 (polymorphic form F), crystal modification 2 (polymorphic form I), and crystal modification 3 (polymorphic form X) of the mono-sodium salt of D-isoglutamyl-D-tryptophan.

BACKGROUND OF THE INVENTION

The compound D-isoglutamyl-D-tryptophan (also known as H-D-γ-Glu-D-Trp-OH or H-D-iGlu-D-Trp-OH or iDD or D-(iEW) or timodepressin or thymodepressin) is a synthetic hemoregulatory dipeptide having the following chemical structure:

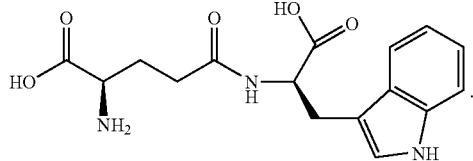

Thymodepressin is the free diacid and has the Chemical Abstracts Service (CAS) Registry Number® 186087-26-3. It is an immunosuppressant and selectively inhibits proliferation of bone marrow cells. It is effective in the suppression of the immune system during the transplantation of the bone marrow, organs and tissues (Semina, O. V et al. (2001) Bulletin of Experimental Biology and Medicine, 131(5), 493-495); the protection of the bone marrow cells and the immune system against the damaging effects of chemotherapy and radiation (U.S. Pat. Nos. 5,736,519, 6,103,699 and 6,410,515); and the treatment of autoimmune diseases, such as psoriasis and atopic dermatitis (Sapuntsova, S. G., et al. (May 2002), Bulletin of Experimental Biology and Medicine, 133 (5), 488-490).

A method for the preparation of thymodepressin was disclosed in example 1 of U.S. Pat. Nos. 5,736,519, 6,103,699 and 6,410,515. However, the manufacture of thymodepressin on a large scale cannot be conducted using the experimental details of this method since a mixture of D-glutamyl-D-tryptophan and D-isoglutamyl-D-tryptophan is produced which must be separated and purified by ion exchange chromatography resulting in a very low yield (12.25%) of thymodepressin.

U.S. Pat. Nos. 5,736,519, 6,103,699 and 6,410,515 teach that the peptides disclosed therein may be converted into acid addition salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and toluenesulphonic acids. However, neither the base addition salts of thymodepressin nor methods for the preparation of such salts are disclosed in these patents.

Thymodepressin is not bioavailable as an oral drug in traditional tablet or capsule form. It is currently being sold in Russia as the di-sodium salt in liquid formulation for injection and intranasal administration for the treatment of psoriasis, atopic dermatitis and rheumatoid arthritis. The solid form of the di-sodium salt of D-isoglutamyl-D-tryptophan is an amorphous powder which is hygroscopic and very difficult to handle. The di-sodium salt of D-isoglutamyl-D-tryptophan has the molecular formula $C_{16}H_{17}N_3Na_2O_5$ and the following chemical structure:

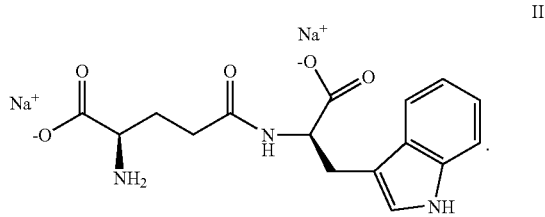

The di-sodium salt of D-isoglutamyl-D-tryptophan is not identified by the CAS Registry System, is not listed in the CAS REGISTRY[SM] File and does not have a CAS Registry Number® associated with it. The identification and structural confirmation of the di-sodium salt of D-isoglutamyl-D-tryptophan has been determined by infrared (IR) spectroscopy (Kashirin, D. M., et al. (2000), Pharmaceutical Chemistry Journal, 34(11), 619-622). However, although the di-sodium salt of D-isoglutamyl-D-tryptophan is known, its preparation, isolation and further characterization has not been disclosed.

Through investigations in our laboratory, we have determined that the freeze-dried di-sodium salt of D-isoglutamyl-D-tryptophan is extremely hygroscopic; turning into a gel in a matter of minutes in air, and thus cannot easily be handled. A powdery or amorphous form of a compound, intended for pharmaceutical use may give rise to manufacturing problems due to bulk density issues, hygroscopicity and variable water content that cannot be corrected by vacuum drying. D-isoglutamyl-D-tryptophan is a dipeptide and the drying of an amorphous form at elevated temperature, for example, 80-100° C. under vacuum is not recommended. Thus, there are serious difficulties experienced during the purification of the di-sodium salt of D-isoglutamyl-D-tryptophan and obtaining the pure di-sodium salt on a manufacturing scale. Further, as discussed above, there is no published procedure for its preparation.

The mono-sodium salt of D-isoglutamyl-D-tryptophan is identified by the CAS Registry System and is listed in the CAS REGISTRY[SM] File with a CAS Registry Number® of 863988-88-9 and has the following chemical structure:

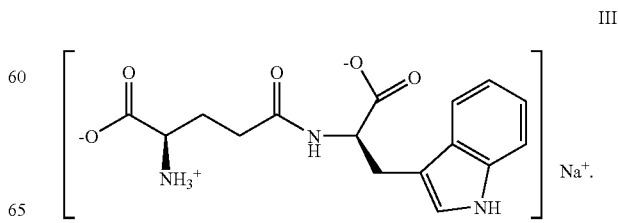

However, there are no references citing the mono-sodium salt of D-isoglutamyl-D-tryptophan and thus no publication of its identity, its physical and/or chemical properties, its characterization in the solid state or a procedure for its preparation and isolation. Therefore, there is no supporting evidence for the existence of the mono-sodium salt of D-isoglutamyl-D-tryptophan.

Freeze-dried powders of mono-sodium and di-sodium salts of peptide drugs may not have controllable powder bulk density ranges for formulation and may require significant investment in freeze-dried dispersion technology.

Therefore, there is a need to develop pharmaceutically acceptable salts of D-isoglutamyl-D-tryptophan which are crystalline. Such crystalline salts can generally be purified more easily than an amorphous form and may possess other advantageous properties, for example in relation to their particular crystalline form and/or their solubility characteristics and/or their lack of hygroscopicity and/or their stability characteristics, including their thermal stability properties and/or their ability to undergo oxidative degradation.

SUMMARY OF THE INVENTION

We have previously invented a process for the manufacture of D-isoglutamyl-D-tryptophan and a crystalline polymorph, a novel stable mono-ammonium salt and a process for the manufacturing of the mono-ammonium salt. This matter was the subject of Canadian Patent Application No. 2,569,204, filed on Nov. 28, 2006, and is incorporated herein by reference. We have also previously invented the calcium, magnesium, potassium, and lithium salts of D-isoglutamyl-D-tryptophan and processes for their manufacture. This matter was the subject of Canadian Patent Application No. 2,571,645, filed on Dec. 19, 2006, and is incorporated herein by reference.

For the production of pharmaceutical dipeptide preparations, it is often advantageous to employ the carboxylic acid group in the form of a specific sodium salt which has, for example, a more favorable solubility, a more favorable absorption behavior, a more favorable stability, a favorable solubility pH, or generally a more favorable property profile.

We have determined that D-isoglutamyl-D-tryptophan can form salts with sodium hydroxide, for example a mono-sodium salt, wherein a hydrogen atom from the carboxylic acid is replaced by a sodium ion which can be formally represented by formula III or a di-sodium salt, wherein two hydrogen atoms are replaced by two sodium salts which can be formally represented by formula II.

We have conducted speciation research and concluded the graphical plots as shown in FIG. 1. We have determined that an advantageous salt for use in pharmaceutical preparations is the mono-sodium salt of the D-isoglutamyl-D-tryptophan, which can be formally represented by formula III, which is the predominant pharmaceutical salt at neutral pH. This takes advantage of the fact that the amino acid is a zwitterion. We have determined that the mono-sodium salt as shown in formula III is the most preferred salt in pharmaceutical preparations. The di-sodium salt of formula II is the predominant species at a pH of about 12 or above. A solution of di-sodium salt in water will have a pH of about 12 and therefore it is unsuitable for use in a liquid formulation. Adjustment of a solution of the di-sodium salt back to a pH of about 7 to about 7.4, in fact produces the mono-sodium salt as the predominant species in solution.

Thus, an object of the present invention is to provide the mono-sodium salt of D-isoglutamyl-D-tryptophan in a form suitable for pharmaceutical use and made by a process suitable for being carried out on a large industrial scale.

A stable crystalline mono-sodium salt can be used in pharmaceutical preparations that are tailored with respect to their composition and the route of administration provide the medicinal effects desired in the specific case.

It has now been determined by us that the mono-sodium salt of the D-isoglutamyl-D-tryptophan can be prepared in a solid crystalline form suitable for pharmaceutical use by reaction of the D-isoglutamyl-D-tryptophan with basic sodium compounds, for example sodium hydroxide. The use of sodium hydride, sodium carbonate, sodium bicarbonate, sodium $C_1$-$C_4$ alkoxides are considered obvious chemical equivalents to sodium hydroxide. Surprisingly, it turned out here that the solid crystalline mono-sodium salt of the D-isoglutamyl-D-tryptophan can occur in a number of different crystal modifications, i.e., in polymorphic forms, which can be prepared specifically by adjustment of the reaction conditions and/or of the crystallization conditions and which differ in their physicochemical properties. Thus, these crystal modifications may differ, for example, in their solubility, rate of dissolution, or behavior during pharmaceutical processing, and allow the production of pharmaceutical preparations having different property profiles starting from a single parent compound.

In accordance with one aspect of the present invention, there is provided the mono-sodium salt of D-isoglutamyl-D-tryptophan in crystalline form.

In another embodiment of the present invention, the crystalline form of the mono-sodium salt of D-isoglutamyl-D-tryptophan produce distinct peaks in a X-ray diffraction measurement having a half-value width below 20 measured at the reflection angle 2 theta using $CuK_\alpha$ radiation.

In another embodiment of the present invention, the crystalline form of the mono-sodium salt of D-isoglutamyl-D-tryptophan is crystal modification 1 (polymorphic form F).

In another embodiment of the present invention, crystal modification 1 (polymorphic form F) of the mono-sodium salt of D-isoglutamyl-D-tryptophan has the XRPD pattern as provided in FIG. 2.

In another embodiment of the present invention, crystal modification 1 (polymorphic form F) of the mono-sodium salt of D-isoglutamyl-D-tryptophan is characterized by peaks in the XRPD pattern having the following 2θ values: 9.23±0.20, 9.91±0.20, 12.41±0.20, 13.76±0.20, 14.87±0.20, 15.75±0.20, 17.88±0.20, 18.78±0.20, 19.57±0.20, 19.84±0.20, 20.31±0.20, 21.32±0.20, 21.55±0.20, 22.95±0.20, 23.45±0.20, 24.34±0.20, 24.96±0.20, 27.49±0.20, 27.94±0.20, 29.27±0.20, 30.07±0.20, 30.43±0.20, 31.29±0.20, 32.25±0.20, 34.07±0.20, 34.94±0.20, 35.53±0.20, 36.08±0.20, 37.21±0.20, 38.17±0.20, 39.19±0.20, and 9.23±0.20.

In another embodiment of the present invention, crystal modification 1 (polymorphic form F) of the mono-sodium salt of D-isoglutamyl-D-tryptophan is characterized by peaks in the XRPD pattern having the following 2θ values: 9.23±0.10, 9.91±0.10, 12.41±0.10, 13.76±0.10, 14.87±0.10, 15.75±0.10, 17.88±0.10, 18.78±0.10, 19.57±0.10, 19.84±0.10, 20.31±0.10, 21.32±0.10, 21.55±0.10, 22.95±0.10, 23.45±0.10, 24.34±0.10, 24.96±0.10, 27.49±0.10, 27.94±0.10, 29.27±0.10, 30.07±0.10, 30.43±0.10, 31.29±0.10, 32.25±0.10, 34.07±0.10, 34.94±0.10, 35.53±0.10, 36.08±0.10, 37.21±0.10, 38.17±0.10, 39.19±0.10, and 9.23±0.10.

In another embodiment of the present invention, crystal modification 1 (polymorphic form F) of the mono-sodium salt of D-isoglutamyl-D-tryptophan is characterized by an XRPD pattern expressed in terms of inter-planar distances d, Bragg's angle 2 theta, and relative intensity (expressed as a percentage with respect to the most intense ray) as follows:

| 2 Theta (°) | D-spacing (Angstrom) | Relative Intensity (%) |
|---|---|---|
| 9.23 | 9.573 | 2 |
| 9.91 | 8.917 | 41.3 |
| 12.41 | 7.126 | 37.6 |
| 13.76 | 6.43 | 0.8 |
| 14.87 | 5.954 | 35.8 |
| 15.75 | 5.622 | 7.6 |
| 17.88 | 4.957 | 5.5 |
| 18.78 | 4.721 | 58.9 |
| 19.57 | 4.532 | 30.9 |
| 19.84 | 4.471 | 28.1 |
| 20.31 | 4.368 | 2.9 |
| 21.32 | 4.165 | 53.5 |
| 21.55 | 4.12 | 30.3 |
| 22.95 | 3.873 | 67.4 |
| 23.45 | 3.79 | 24.5 |
| 24.34 | 3.654 | 19.4 |
| 24.96 | 3.565 | 85.2 |
| 27.49 | 3.242 | 100 |
| 27.94 | 3.19 | 23.3 |
| 29.27 | 3.049 | 19.1 |
| 30.07 | 2.97 | 27.2 |
| 30.43 | 2.935 | 15.2 |
| 31.29 | 2.856 | 39.9 |
| 32.25 | 2.774 | 13 |
| 34.07 | 2.629 | 19.3 |
| 34.94 | 2.566 | 7.8 |
| 35.53 | 2.525 | 5 |
| 36.08 | 2.487 | 8.4 |
| 37.21 | 2.414 | 15.5 |
| 38.17 | 2.356 | 9.1 |
| 39.19 | 2.297 | 3.1 |

In another embodiment of the present invention, the crystalline form of the mono-sodium salt of D-isoglutamyl-D-tryptophan is crystal modification 2 (polymorphic form I).

In another embodiment of the present invention, crystal modification 2 (polymorphic form I) of the mono-sodium salt of D-isoglutamyl-D-tryptophan has the XRPD pattern provided in FIG. 3.

In another embodiment of the present invention, crystal modification 2 (polymorphic form I) of the mono-sodium salt of D-isoglutamyl-D-tryptophan is characterized by peaks in the XRPD pattern having the following 2θ values: 9.65±0.20, 10.41±0.20, 11.2±0.20, 11.71±0.20, 13.45±0.20, 13.93±0.20, 14.44±0.20, 15.61±0.20, 17.01±0.20, 18.18±0.20, 18.65±0.20, 20.02±0.20, 20.85±0.20, 21.39±0.20, 21.73±0.20, 22.52±0.20, 23.27±0.20, 24.3±0.20, 25.84±0.20, 26.82±0.20, 28.49±0.20, 30.18±0.20, 30.76±0.20, 31.49±0.20, 33.03±0.20, 34.55±0.20, 34.97±0.20, 35.74±0.20, 37.25±0.20, 37.71±0.20, and 38.79±0.20.

In another embodiment of the present invention, crystal modification 2 (polymorphic form I) of the mono-sodium salt of D-isoglutamyl-D-tryptophan is characterized by peaks in the XRPD pattern having the following 2θ values: 9.65±0.10, 10.41±0.10, 11.2±0.10, 11.71±0.10, 13.45±0.10, 13.93±0.10, 14.44±0.10, 15.61±0.10, 17.01±0.10, 18.18±0.10, 18.65±0.10, 20.02±0.10, 20.85±0.10, 21.39±0.10, 21.73±0.10, 22.52±0.10, 23.27±0.10, 24.3±0.10, 25.84±0.10, 26.82±0.10, 28.49±0.10, 30.18±0.10, 30.76±0.10, 31.49±0.10, 33.03±0.10, 34.55±0.10, 34.97±0.10, 35.74±0.10, 37.25±0.10, 37.71±0.10, and 38.79±0.10.

In another embodiment of the present invention, crystal modification 2 (polymorphic form I) of the mono-sodium salt of D-isoglutamyl-D-tryptophan is characterized by an XRPD pattern expressed in terms of inter-planar distances d, Bragg's angle 2 theta, and relative intensity (expressed as a percentage with respect to the most intense ray) as follows:

| 2-Theta (°) | D-spacing (Angstrom) | Relative Intensity (%) |
|---|---|---|
| 9.65 | 9.161 | 5.3 |
| 10.41 | 8.492 | 23.7 |
| 11.2 | 7.897 | 40.4 |
| 11.71 | 7.549 | 4.5 |
| 13.45 | 6.58 | 90.2 |
| 13.93 | 6.351 | 15.9 |
| 14.44 | 6.128 | 3.7 |
| 15.61 | 5.672 | 32.4 |
| 17.01 | 5.207 | 9.9 |
| 18.18 | 4.876 | 11.7 |
| 18.65 | 4.755 | 47.8 |
| 20.02 | 4.432 | 59.2 |
| 20.85 | 4.257 | 35.9 |
| 21.39 | 4.15 | 24.1 |
| 21.73 | 4.086 | 27.3 |
| 22.52 | 3.945 | 100 |
| 23.27 | 3.819 | 13.7 |
| 24.3 | 3.66 | 32.4 |
| 25.84 | 3.445 | 69.5 |
| 26.82 | 3.322 | 82.5 |
| 28.49 | 3.13 | 30.1 |
| 30.18 | 2.959 | 58.8 |
| 30.76 | 2.904 | 86.9 |
| 31.49 | 2.839 | 35.3 |
| 33.03 | 2.71 | 8.7 |
| 34.55 | 2.594 | 17.8 |
| 34.97 | 2.564 | 43.4 |
| 35.74 | 2.51 | 8.5 |
| 37.25 | 2.412 | 28.1 |
| 37.71 | 2.383 | 28.5 |
| 38.79 | 2.319 | 16.9 |

In another embodiment of the present invention, the crystalline form of the mono-sodium salt of D-isoglutamyl-D-tryptophan is crystal modification 3 (polymorphic form X).

In another embodiment of the present invention, crystal modification 3 (polymorphic form X) of the mono-sodium salt of D-isoglutamyl-D-tryptophan has the XRPD pattern provided in FIG. 4.

In another embodiment of the present invention, crystal modification 3 (polymorphic form X) of the mono-sodium salt of D-isoglutamyl-D-tryptophan is characterized by peaks in the XRPD pattern having the following 2θ values: 9.187±0.200, 11.058±0.200, 11.713±0.200, 12.239±0.200, 13.785±0.200, 14.806±0.200, 15.763±0.200, 17.126±0.200, 17.693±0.200, 18.268±0.200, 18.562±0.200, 19.261±0.200, 20.033±0.200, 20.63±0.200, 21.006±0.200, 21.778±0.200, 22.268±0.200, 23.054±0.200, 23.361±0.200, 23.851±0.200, 24.626±0.200, 24.981±0.200, 25.507±0.200, 26.257±0.200, 26.963±0.200, 27.329±0.200, 27.807±0.200, 28.243±0.200, 28.975±0.200, 29.264±0.200, 29.687±0.200, 30.409±0.200, 30.798±0.200, 31.193±0.200, 31.724±0.200, 32.505±0.200, 32.985±0.200, 33.645±0.200, 34.249±0.200, 34.587±0.200, 35.048±0.200, 35.41±0.200, 35.933±0.200, 36.833±0.200, 37.276±0.200, 37.937±0.200, 38.467±0.200, and 39±0.200.

In another embodiment of the present invention, crystal modification 3 (polymorphic form X) of the mono-sodium salt of D-isoglutamyl-D-tryptophan is characterized by peaks in the XRPD pattern having the following 2θ values: 9.187±0.100, 11.058±0.100, 11.713±0.100, 12.239±0.100, 13.785±0.100, 14.806±0.100, 15.763±0.100, 17.126±0.100, 17.693±0.100, 18.268±0.100, 18.562±0.100, 19.261±0.100, 20.033±0.100, 20.63±0.100, 21.006±0.100, 21.778±0.100, 22.268±0.100, 23.054±0.100, 23.361±0.100, 23.851±0.100, 24.626±0.100, 24.981±0.100, 25.507±0.100, 26.257±0.100, 26.963±0.100, 27.329±0.100, 27.807±0.100, 28.243±0.100, 28.975±0.100, 29.264±0.100, 29.687±0.100, 30.409±0.100, 30.798±0.100, 31.193±0.100, 31.724±0.100, 32.505±0.100, 32.985±0.100, 33.645±0.100, 34.249±0.100, 34.587±0.100, 35.048±0.100, 35.41±0.100, 35.933±0.100, 36.833±0.100, 37.276±0.100, 37.937±0.100, 38.467±0.100, and 39±0.100.

In another embodiment of the present invention, crystal modification 3 (polymorphic form X) of the mono-sodium salt of D-isoglutamyl-D-tryptophan is characterized by an XRPD pattern expressed in terms of inter-planar distances d, Bragg's angle 2 theta, and relative intensity (expressed as a percentage with respect to the most intense ray) as follows:

| 2-Theta (°) | D-spacing (Angstrom) | Relative Intensity (%) |
|---|---|---|
| 9.187 | 9.618 | 25.4 |
| 11.058 | 7.995 | 2.3 |
| 11.713 | 7.549 | 18.7 |
| 12.239 | 7.226 | 34.2 |
| 13.785 | 6.419 | 23.5 |
| 14.806 | 5.978 | 13 |
| 15.763 | 5.618 | 5 |
| 17.126 | 5.173 | 29.3 |
| 17.693 | 5.009 | 8.4 |
| 18.268 | 4.852 | 48.2 |
| 18.562 | 4.776 | 28.2 |
| 19.261 | 4.604 | 14.3 |
| 20.033 | 4.429 | 14.5 |
| 20.63 | 4.302 | 17.2 |
| 21.006 | 4.226 | 12 |
| 21.778 | 4.078 | 2.4 |
| 22.268 | 3.989 | 100 |
| 23.054 | 3.855 | 6.4 |
| 23.361 | 3.805 | 7.4 |
| 23.851 | 3.728 | 1.8 |
| 24.626 | 3.612 | 14.9 |
| 24.981 | 3.562 | 14.7 |
| 25.507 | 3.489 | 11.1 |
| 26.257 | 3.391 | 34.3 |
| 26.963 | 3.304 | 11.1 |
| 27.329 | 3.261 | 20.6 |
| 27.807 | 3.206 | 35 |
| 28.243 | 3.157 | 25.6 |
| 28.975 | 3.079 | 1.1 |
| 29.264 | 3.049 | 2.3 |
| 29.687 | 3.007 | 9.5 |
| 30.409 | 2.937 | 20.9 |
| 30.798 | 2.901 | 6.1 |
| 31.193 | 2.865 | 6.9 |
| 31.724 | 2.818 | 24.7 |
| 32.505 | 2.752 | 8 |
| 32.985 | 2.713 | 12.1 |
| 33.645 | 2.662 | 26.5 |
| 34.249 | 2.616 | 15.2 |
| 34.587 | 2.591 | 8.6 |
| 35.048 | 2.558 | 4.6 |
| 35.41 | 2.533 | 3.3 |
| 35.933 | 2.497 | 15.3 |
| 36.833 | 2.438 | 8 |
| 37.276 | 2.41 | 10.8 |
| 37.937 | 2.37 | 12.7 |
| 38.467 | 2.338 | 14.7 |
| 39 | 2.308 | 2.6 |

In another embodiment of the present invention, the crystalline form of the mono-sodium salt of D-isoglutamyl-D-tryptophan is a mixture of crystal modifications 1 (polymorphic form F) and 2 (polymorphic form I) of the mono-sodium salt of D-isoglutamyl-D-tryptophan.

In another embodiment of the present invention, the crystalline form of the mono-sodium salt of D-isoglutamyl-D-tryptophan is a mixture of the crystal modifications 1 (polymorphic form F) and 3 (polymorphic form X) of the mono-sodium salt of D-isoglutamyl-D-tryptophan.

In another embodiment of the present invention, the mixture of the crystal modifications 1 (polymorphic form F) and 3 (polymorphic form X) of the mono-sodium salt of D-isoglutamyl-D-tryptophan has the XRPD pattern provided in FIG. 9.

In accordance with another aspect of the present invention, there is provided a pharmaceutical composition comprising any of the crystalline forms of the mono-sodium salt of D-isoglutamyl-D-tryptophan described above, together with at least one pharmaceutically acceptable carrier.

In accordance with another aspect of the present invention, there is provided a process for making a pharmaceutical composition comprising any of the crystalline forms of the mono-sodium salt of D-isoglutamyl-D-tryptophan described above, wherein said process comprises combining any of the crystalline forms of the mono-sodium salt of D-isoglutamyl-D-tryptophan as described above, with at least one pharmaceutically acceptable carrier.

In accordance with another aspect of the present invention, there is provided a use of any of the crystalline forms of the mono-sodium salt of D-isoglutamyl-D-tryptophan described above, without chromatographic purification in the manufacture of a pharmaceutical composition.

In accordance with another aspect of the present invention, there is provided a use of any of the crystalline forms of the mono-sodium salt of D-isoglutamyl-D-tryptophan as an anti-psoriasis agent.

In accordance with another aspect of the present invention, there is provided a process for the preparation of the mono-sodium salt of D-isoglutamyl-D-tryptophan in crystalline form, comprising the steps of:
  (a) preparing a solution of D-isoglutamyl-D-tryptophan and sodium hydroxide in water at a pH of about 6.5 to about 7.2;
  (b) filtering the solution to remove solid particulates;
  (c) evaporating the water to concentrate the filtrate; and
  (d) adding isopropanol to precipitate the mono-sodium salt of D-isoglutamyl-D-tryptophan,
or
  (e) stirring the solid obtained from process steps (a), (b), (c), and (d) with ethyl acetate; and
  (f) filtering the solid,
or
  steps (a) and (b) as described above, followed by steps:
  (g) evaporating the filtrate from step (b) to give a solid;
  (h) adding water to obtain a solution of the mono-sodium salt of D-isoglutamyl-D-tryptophan; and
  (i) evaporating the water over a period of more than about 5 hrs to give the mono-sodium salt of D-isoglutamyl-D-tryptophan in crystalline form,
or
  (j) preparing a solution of the mono-sodium salt of D-isoglutamyl-D-in methanol;
  (k) filtering the solution to remove solid particulates; and
  (l) adding isopropanol to precipitate the mono-sodium salt of D-isoglutamyl-D-tryptophan,
or
  (m) preparing a solution of the mono-ammonium salt of D-isoglutamyl-D-tryptophan and sodium hydroxide in water, followed by steps (b), (c) and (d) as described above.

In an embodiment of the present invention, wherein the process comprises steps (a), (b), (c) and (d), the stirring time in step (d) is from about 1.5 to about 16 hrs.

In another embodiment of the present invention, wherein the process comprises steps (a), (b), (c) and (d), the stirring time in step (d) is about 1 hr.

In another embodiment of the present invention, wherein the process comprises steps (a), (b), (c), (d), (e) and (f), the stirring time in step (d) is about 1 hr and the stirring time in ethyl acetate in step (f) is about 2.5 hrs.

In another embodiment of the present invention, wherein the process comprises steps (a), (b), (g), (h) and (i), from about 18 to about 22 ml of water is added per gm of the mono-sodium salt of D-isoglutamyl-D-tryptophan in step (h) and the evaporation time in step (i) is from about 5 to about 6 hours and the temperature of evaporation is from about 30 to about 35° C.

In another embodiment of the present invention, wherein the process comprises steps (j), (k), and (l), the ratio of the mono-sodium salt of D-isoglutamyl-D-tryptophan is 1 gm per about 11 to about 13 ml methanol in step a) and the ratio of isopropanol to methanol in step (l) is from about 0.4 to 0.6 ml to about 1 ml.

In another embodiment of the present invention, wherein the process comprises steps (m), (b), (c) and (d), the stirring time in step (d) is from about 12 to about 16 hours.

Other and further advantages and features of the present invention will be apparent to those skilled in the art from the following g detailed description thereof taken in conjunction with the accompanying drawings.

DETAIL DESCRIPTION OF INVENTION

As used herein, D-isoglutamyl-D-tryptophan is the dipeptide

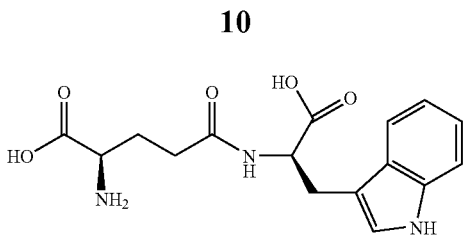

The chemistry of amino acids or simple dipeptides is complicated by the fact that the —$NH_2$ group is a base and the —$CO_2H$ group is an acid. In aqueous solution, an $H^+$ ion is therefore transferred from one end of the molecule to the other to form zwitterions.

Zwitterions are simultaneously electrically charged and electrically neutral. They contain positive and negative charges, but the net charge on the molecule is zero. Although the basis for salt formation is not entirely bound by theory, the iGlu amino acid unit of H-D-iGlu-D-Trp-OH exists as a zwitterion, and therefore only one —$CO_2H$ group is left that is available for the formation of a salt when only one equivalent of monovalent sodium hydroxide is used to adjust the pH to neutral conditions. When H-D-iGlu-D-Trp-OH mono-sodium salt of formula III is drawn in the format shown above, only one $CO_2H$ group can accommodate one mono-sodium metal to give the salt of formula III. In the compound of formula (III), a sodium cation displaces one hydrogen atom, on the carboxylic acid portion of the compound of formula (I).

Figure 1:
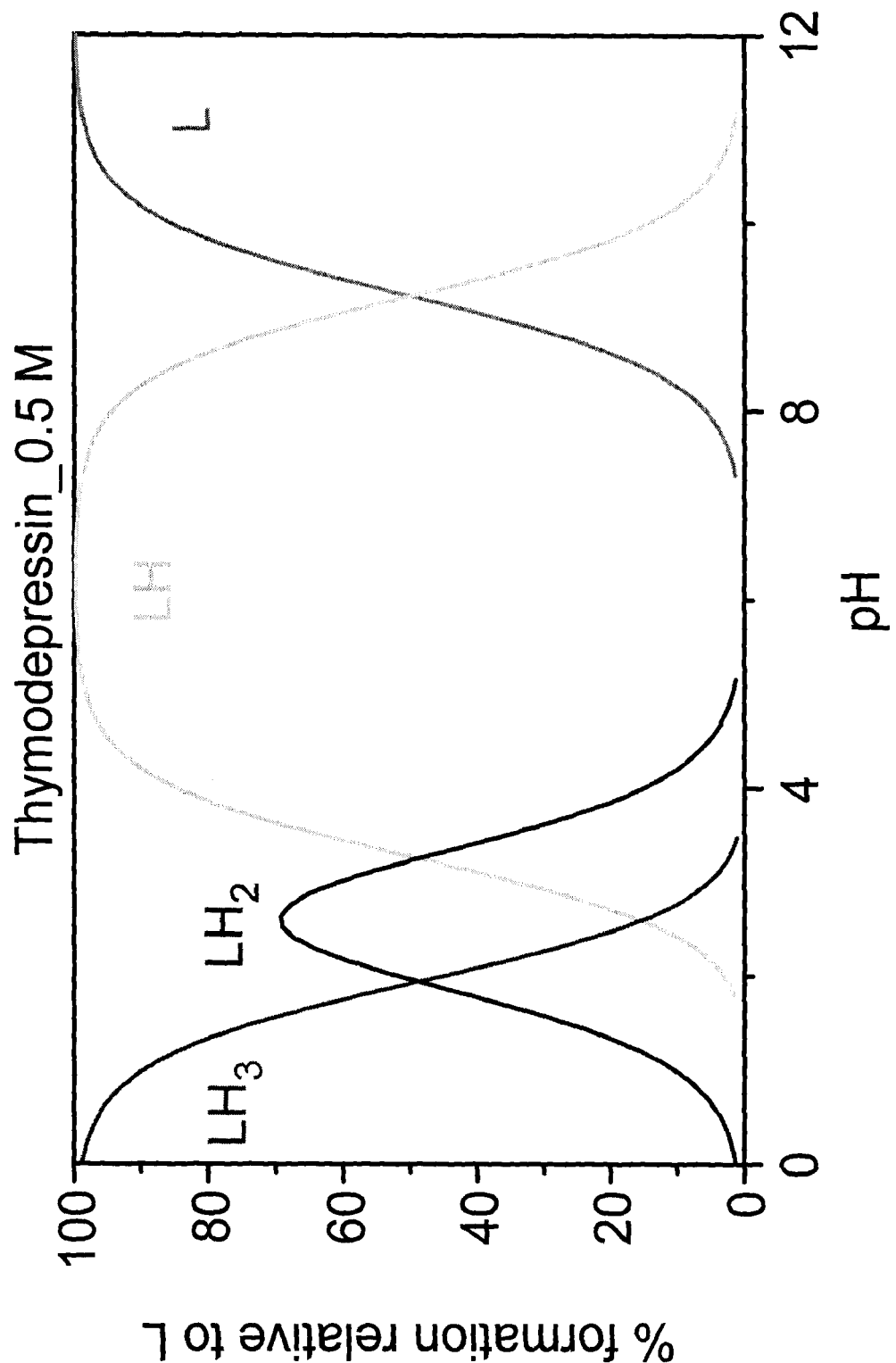
FIG. 1 is a speciation plot of the dipeptide H-D-iGlu-D-Trp-OH and its salt calculated using experimentally determined pKas of the acid and amine groups.

FIG. 1 is a speciation plot of the dipeptide H-D-iGlu-D-Trp-OH and its salt calculated with the software Hyperquad Simulation & Speciation using experimentally determined pKas of the acid and amine groups. $LH_2$=H-D-iGlu-D-Trp-OH in diacid form represented by a compound of formula I, LH=mono carboxylic acid salt such as the mono-sodium salt represented by a compound of formula III, L=dicarboxylic acid salt such as the di-sodium salt represented by a compound of formula II, $LH_3$=acid addition salt of H-D-iGlu-D-Trp-OH such as the mono hydrochloride salt of a compound of formula I wherein the $NH_2$ is protonated. The X axis provides the pH of the solution. The Y axis reports the molar fraction of the species present at a particular pH. Note: % formation relative to L is the default terminology of the software. The concentration of 0.5M is used to reflect the equivalency of 1 gm of thymodepressin in 6 ml water during isolation purposes. This figure shows that about 100% of the thymodepressin is in the mono-sodium salt form in water at a pH of about 7.0 to about 7.4.

The present invention is directed to the novel mono-sodium salt of D-isoglutamyl-D-tryptophan of formula (III), novel crystalline forms of the mono-sodium salt of D-isoglutamyl-D-tryptophan, including novel crystal modification 1 (polymorphic form F), novel crystal modification 2 (polymorphic form I), and novel crystal modification 3 (polymorphic form X).

The present invention is also directed to a process for the preparation of the novel crystal modification 1 (polymorphic form F), the novel crystal modification 2 (polymorphic form I), the novel crystal modification 3 (polymorphic form X), and a mixture of the novel crystal modifications 1 and 3 of the mono-sodium salt of D-isoglutamyl-D-tryptophan, wherein the process comprises the steps of:
- (a) preparing a solution of D-isoglutamyl-D-tryptophan and sodium hydroxide in water at a pH from about 6.5 to about 7.0;
- (b) filtering the solution to remove solid particulates;
- (c) evaporating the water to concentrate the filtrate; and
- (d) adding isopropanol to precipitate the mono-sodium salt of D-isoglutamyl-D-tryptophan, or steps (a), (b), (c), and (d) as described above, followed by the steps of:
- (e) stirring the solid obtained from step (d) with ethyl acetate; and
- (f) filtering of the solid, or steps (a) and (b) as described above, followed by the steps of:
- (g) evaporating the filtrate from step (b) to give a solid;
- (h) adding water to obtain a solution of the mono-sodium salt of D-isoglutamyl-D-tryptophan; and
- (i) evaporating the water over a period of more than about 5 hrs to give the mono-sodium salt of D-isoglutamyl-D-tryptophan in crystalline form, or

- (j) preparing a solution of the mono-sodium salt of D-isoglutamyl-D- in methanol;
- (k) filtering the solution to remove solid particulates; and
- (l) adding isopropanol to precipitate the mono-sodium salt of D-isoglutamyl-D-tryptophan, or

- (m) preparing a solution of the mono-ammonium salt of D-isoglutamyl-D-tryptophan and sodium hydroxide in water, followed by steps (b), (c) and (d) as described above.

Preferably, the process comprising steps (a), (b), (c) and (d) as described above is used to prepare the crystal modification 1 (polymorphic form F) and the crystal modification 2 (polymorphic form I) of the mono-sodium salt of D-isoglutamyl-D-tryptophan. The process comprises the steps of:
- (a) preparing a solution of D-isoglutamyl-D-tryptophan and sodium hydroxide in water;
- (b) filtering the solution to remove solid particulates;
- (c) evaporating the water to concentrate the filtrate; and
- (d) adding isopropanol to precipitate the mono-sodium salt of D-isoglutamyl-D-tryptophan.

Depending on the volume ratio of isopropanol to the solution of mono-sodium salt of D-isoglutamyl-D-tryptophan and its concentration and the stirring time, pure crystal modification 1 or pure crystal modification 2 can be obtained by this process. Based on speciation plot calculations as provided in FIG. 1, the pH of the solution from step (a) should be at a pH of about 6.5 to about 7.2, preferably at a pH of about 7.0, before proceeding to step (b).

A solution of D-isoglutamyl-D-tryptophan and sodium hydroxide in water is prepared by adding solid D-isoglutamyl-D-tryptophan to sodium hydroxide solution. D-isoglutamyl-D-tryptophan has limited solubility in water (<20 mg per ml in water), but the sodium salt is extremely soluble in water. Sodium hydroxide is chosen based on the convenience in obtaining sodium hydroxide solution, however other sodium bases such as sodium hydride, sodium carbonate, sodium bicarbonate can be used. These chemicals are obvious chemical equivalents to sodium hydroxide for step (a) of the process. In step (b), the solution is filtered to remove any particulates prior to proceeding to step (c).

In the process for the preparation of crystal modification 1, the filtrate from step (b) is then concentrated to remove water to reach an estimated concentration of about 1.3 to about 3 mmol/ml of the solute in solution in step (c). The solute is the mono-sodium salt of D-isoglutamyl-D-tryptophan. An anti-solvent is used to precipitate the mono-sodium salt. As used herein, an anti-solvent is a solvent that can cause the precipitation of a solute in solution. Examples of an anti-solvent for use in the present invention are isopropanol and $C_1$-$C_4$ alkanol. In a preferred embodiment, isopropanol is used as an anti-solvent to precipitate the mono-sodium salt. In step (d), about 30 to about 40 ml of isopropanol per ml of the sodium salt of isoglutamyl-D-tryptophan in water is added to initiate the precipitation of the crystal modification 1 of the mono-sodium salt of D-isoglutamyl-D-tryptophan. The stirring time is from about 1.5 to about 16 hrs, preferably from about 12 to about 16 hrs. The solid is isolated by filtration and dried under high vacuum in a vacuum oven. The preferred temperature of drying is from about 40 to about 45° C., and the preferred vacuum setting is below about 8 mm Hg. Still preferred, the applied vacuum is below about 5 mm Hg.

In the process for the preparation of crystal modification 2, the filtrate from step (b) is then concentrated to remove water in step (c) to reach an estimated concentration of about 3 to about 18 mmol/ml of the solute in solution. The solute is the mono-sodium salt of D-isoglutamyl-D-tryptophan. Isopropanol is used as an anti-solvent to precipitate the mono-sodium salt. About 40 ml of isopropanol per ml of the mono-sodium salt of D-isoglutamyl-D-tryptophan in water is added to precipitate the crystal modification 2 of the mono-sodium salt of D-isoglutamyl-D-tryptophan. The stirring time is about 1 hour. The solid is isolated by filtration and dried under high vacuum in a vacuum oven. The preferred temperature of drying is from about 40 to about 45° C., and the preferred vacuum setting is below about 8 mm Hg. Still preferred, the applied vacuum is below about 5 mm Hg.

Although not bound by theory, we have determined that in the isopropanol precipitation reaction in step (d), the stirring time plays an important role in determining the crystal modification 1 or 2 as the product of the reaction. A short stirring time of about one hour or less than about one hour results in crystal modification 2 (polymorphic form I), while a long stirring time of up to about 16 hours resulted in the crystal modification 1 (polymorphic form F). The outcome of the crystal modification also depends on the concentration of the mono-sodium salt in solution and the amount of isopropanol added as an anti-solvent. Details of the experimental conditions can be found in Examples 1 and 2 described below.

We have also found that when a solution of mono-sodium salt of formula III in water is precipitated with isopropanol at about 3 mmol/ml concentration, a mixture of crystal modification 1 (polymorphic form F) and crystal modification 3 (polymorphic form X) can be obtained. When this mixture is stirred with ethyl acetate and then filtered, the majority of the crystalline form is the crystal modification 1 and the experimental information is provided in Example 4B described in more detail below.

Therefore, preferably, a process for producing the crystal modification 1 (polymorphic form F) of the mono-sodium salt of D-isoglutamyl-D-tryptophan comprises the following steps:
- (a) preparing a solution of D-isoglutamyl-D-tryptophan and sodium hydroxide in water at a pH of about 6.5 to about 7.0;
- (b) filtering the solution to remove solid particulates;
- (c) evaporating the water to concentrate the filtrate;

(d) adding isopropanol to precipitate the mono-sodium salt of D-isoglutamyl-D-tryptophan;

(e) stirring the solid obtained in step (d) with ethyl acetate; and (f) filtering of the solid.

The presence of crystal modification 3 (polymorphic form X) in a mixture with crystal modification 1 (polymorphic form F) required further research which lead to the invention of two processes for the preparation of crystal modification 3.

Preferably, the process comprising steps (a), (b), (g), (h) and (i) as described above is used to prepare the crystal modification 3 (polymorphic form X) of the mono-sodium salt of D-isoglutamyl-D-tryptophan. The process comprises the steps of:

(a) preparing a solution of D-isoglutamyl-D-tryptophan and sodium hydroxide in water at a pH of about 6.5 to about 7.2;

(b) filtering the solution to remove solid particulates;

(g) evaporating the filtrate from step (b) to give a solid;

(h) adding water to obtain a solution of the mono-sodium salt of D-isoglutamyl-D-tryptophan; and (i) evaporating the water over a period of more than about 5 hrs to give the mono-sodium salt of D-isoglutamyl-D-tryptophan in crystalline form.

Steps (a) and (b) are carried out as those described above. In step (g), about 18 to about 22 ml of water is added per gm of the mono-sodium salt of D-isoglutamyl-D-tryptophan to prepare the solution. Slow solvent evaporation under reduced pressure affords the crystal modification 3 (polymorphic form X) of the mono-sodium salt of D-isoglutamyl-D-tryptophan. In step (h), the solvent evaporation is conducted in a round bottom flask using a rotor evaporator under vacuum. The preferred temperature of the external water bath for the solvent evaporation is about 30 to about 35° C., the preferred vacuum is about 14 to about 20 mm Hg, and the preferred time period of evaporation is about 5 to about 7 hrs.

Alternatively but also preferably, the process comprising steps (j), (k), and (l) is used to prepare crystal modification 3 (polymorphic form X) of the mono-sodium salt of D-isoglutamyl-D-tryptophan. The process comprises the steps of:

(j) preparing a solution of the mono-sodium salt of D-isoglutamyl-D-tryptophan in methanol;

(k) filtering the solution to remove solid particulates; and (l) adding isopropanol to precipitate the mono-sodium salt of D-isoglutamyl-D-tryptophan.

In step (j), a solution of the mono-sodium salt of D-isoglutamyl-D-tryptophan in methanol is prepared by dissolving the solid mono-sodium salt (in any polymorphic form) in methanol. Heating of the suspension in methanol is required to facilitate dissolution. The preferred concentration of the solute (mono-sodium salt) to methanol is 1 gm solute per about 11 to about 13 ml of methanol. The insoluble particulates are then filtered in step (k). About 0.4 to about 0.6 ml of isopropanol is added to per ml of the methanol solution from step (l). The insoluble material is isolated by suction filtration, and is the crystal modification 3 (polymorphic form X) of the mono-sodium salt of D-isoglutamyl-D-tryptophan.

In another embodiment of the present invention, the mono-sodium salt of D-isoglutamyl-D-tryptophan can be prepared by salt exchange reaction between the mono-ammonium salt of D-isoglutamyl-D-tryptophan and sodium hydroxide. The process comprises steps (m), (b), (c) and (d) as described above and as follows:

(m) preparing a solution of the mono-ammonium salt of D-isoglutamyl-D-tryptophan and sodium hydroxide in water;

(b) filtering the solution to remove solid particulates;

(c) evaporating the water to concentrate the filtrate; and (d) adding isopropanol to precipitate the mono-sodium salt of D-isoglutamyl-D-tryptophan.

In step (m), the mono-ammonium salt of D-isoglutamyl-D-tryptophan and sodium hydroxide is mixed in roughly about 1:1 ratio in water. The solution is filtered in step (b). It should be noted that in step (m), ammonium hydroxide is released. Therefore, the pH of the solution is higher than a pH of about 7.5. No pH adjustment is required. The filtrate is concentrated to an estimated concentration of about 0.25 to about 0.5 gm solute (mono-sodium salt) in per ml of water. In step (d), about 15 to about 30 ml of isopropanol is added to per ml of the solution from step (c) to precipitate the crystal modification 1 (polymorphic form F) of the mono-sodium salt of D-isoglutamyl-D-tryptophan.

As described in Example 4 of the present invention, the mixed polymorph of the mono-sodium salt containing the crystal modifications 1 and 3 can also be obtained from the reaction of D-isoglutamyl-D-tryptophan with sodium hydroxide by varying the conditions. As part of the present invention, we have illustrated the conversion of a mixture of crystal modifications 1 and 3 to mainly crystal modification 1 in Example 4 by stirring the solid in ethyl acetate.

As generally illustrated above for the preparation of the mono-sodium salt of the D-isoglutamyl-D-tryptophan, it can be advantageous when carrying out this process as well as the other processes described to additionally add isopropanol to the aqueous solution of the sodium salt for the isolation of the sodium salt crystalline solid.

Although not bound by theory, a short stirring time, normally about one hour or less, with isopropanol produces the crystal modification 2 (polymorphic form I) of the mono-sodium salt of formula III. A long stirring time, up to about 16 hrs produces the crystal modification 1 (polymorphoric form F). In cases when a mixture of the crystal modification 1 (polymorphoric form F) and the crystal modification 3 (polymorphoric form X) are produced, pure crystal modification 1 can be produced by stirring in ethyl acetate.

When a solution of the mono-sodium salt is prepared in methanol, the use of isopropanol as an anti-solvent affords the crystal modification 3 of the present invention.

The pharmacological properties of the crystalline mono-sodium salt of D-isoglutamyl-D-tryptophan and crystal modifications 1, 2, and 3 and their possible uses for the therapy and prophylaxis of disorders correspond, if the substances are present in the target organ or in the target cell in dissolved form independent of the original form of the solid, to those described for thymodepressin and its disodium salt, which are described in, among others, U.S. Pat. Nos. 5,736, 519, 6,103,699 and 6,410,5151 Semina, O. V et al. (2001), Bulletin of Experimental Biology and Medicine, 131(5), 493-495); and Sapuntsova, S. G., et al. (May 2002), Bulletin of Experimental Biology and Medicine, 133(5), 488-490).

The action of crystal modifications 1, 2, and 3 can be investigated, for example, in the pharmacological models which are described in, among others, U.S. Pat. Nos. 5,736, 519, 6,103,699 and 6,410,515; Semina, O. V et al. (2001), Bulletin of Experimental Biology and Medicine, 131(5), 493-495); and Sapuntsova, S. G., et al. (May 2002), Bulletin of Experimental Biology and Medicine, 133(5), 488-490), which are incorporated herein by reference and the respective contents of which are part of the present disclosure.

The crystal modifications of the mono-sodium salt of D-isglutamyl-D-tryptophan according to the present invention can thus be used in animals, preferably in mammals, and in particular in humans as pharmaceuticals on their own, in mixtures with one another, or in the form of pharmaceutical preparations (or pharmaceutical compositions). The present invention therefore also relates to the crystalline mono-sodium salt of the D-isoglutamyl-D-tryptophan and the crystal modifications of the mono-sodium salt of the D-isoglutamyl-D-tryptophan for use as pharmaceuticals, their use as anti-psoriasis agents, and in particular their use as an immunosuppressant, and also their use for the production of medicaments thereof. The present invention furthermore relates to pharmaceutical preparations which contain, as active constituents, an efficacious dose of the crystalline mono-sodium salt of the D-isoglutamyl-D-tryptophan, in particular of the mono-sodium salt of the D-isoglutamyl-D-tryptophan in the form of one or more of the crystal modifications 1, 2, and 3, and at least one pharmaceutically acceptable carrier, that is one or more vehicles and/or excipients. These pharmaceutical preparations contain, for example, the mono-sodium salt of the D-isoglutamyl-D-tryptophan in crystal modification 1 and at least one pharmaceutically acceptable carrier, or the mono-sodium salt of D-isoglutamyl-D-tryptophan in crystal modification 2 and at least one pharmaceutically acceptable carrier, or the mono-sodium salt of D-isoglutamyl-D-tryptophan in crystal modification 3 and at least one pharmaceutically acceptable carrier, or, for example, two of the crystal modifications according to the present invention such as crystal modifications 1 and 2, or crystal modifications 1 and 3, or crystal modifications 2 and 3, in each case together with at least one pharmaceutically acceptable carrier.

Utility and Administration

The di-sodium salt of D-isoglutamyl-D-tryptophan has been used for the treatment of psoriasis, atopic dermatitis and rheumatoid arthritis. Therefore the mono-sodium salt of D-isoglutamyl-D-tryptophan of this invention may be formulated into pharmaceutical compositions for administration to subjects in a therapeutically active amount and in a biologically compatible form suitable for in vivo administration, i.e. a form of the peptides to be administered in which any toxic effects are outweighed by the therapeutic effects.

According to the speciation plot as shown in FIG. 1, the dominant species at neutral pH is the mono carboxylate form of thymodepressin, that is, the mono-sodium salt of the dipeptide D-isoglutamyl-D-tryptophan, if the counterion is sodium. The di-sodium salt of D-isoglutamyl-D-tryptophan is extremely hygroscopic and is very difficult to handle for dispensing purposes. Depending on its concentration, the pH of a solution of di-sodium salt is more than about 8.2. A solution containing 100% of the di-sodium salt has pH of greater than about 11.5 as per speciation plot (FIG. 1). The high pH is unsuitable for dosing to human as a solution. pH adjustment from about 7.2 to about 7.4 with mineral acid introduces additional salt, for example, sodium chloride into the formulation.

The crystalline forms of the mono-sodium salt are ideal candidates to replace the di-sodium salt in the preparation of different formulations. Administration of the novel crystalline salts of this invention as described herein can be via any of the accepted modes of administration for systemically active therapeutic medicaments. These methods include oral, parenteral and otherwise systemic, aerosol or topical forms.

Depending on the intended mode of administration, the compositions used may be in the form of solid, semi-solid or liquid dosage forms, such as, for example, tablets, sublingual tablets, suppositories, pills, capsules, powders, liquids, aerosols, suspensions, or the like, preferably in unit dosage forms suitable for single administration of precise dosages. The compositions will include at least one conventional pharmaceutical carrier or excipient and crystalline mono-sodium D-isoglutamyl-D-tryptophan and, in addition, may include other medicinal agents, pharmaceutical agents, carriers, adjuvants, etc.

For solid compositions, conventional non-toxic solid carriers includes, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, propylene glycol, as the carrier. Liquid pharmaceutically administerable compositions can, for example, be prepared by dissolving, dispersing, etc., an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington: The Science and Practice of Pharmacy, $21^{st}$ Edition, 2006, Part 5, Pharmaceutical Manufacturing, Chapters 37, 39, 41-47 and 50, pp. 702-719, 745-775, 802-938, and 1000-1017 (formerly known as Remington's Pharmaceutical Sciences), David B. Troy (Ed.), Lipincott Williams & Wilkins, Baltimore, Md. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For the mono-sodium salt of D-isoglutamyl-D-tryptophan, either oral or nasal (bronchial) administration is preferred, depending on the nature of the disorder being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like.

Such compositions take the form of solutions, suspensions, tablets, pills, capsules, powders, sustained release formulations and the like. Such compositions may contain from about 1% to about 95% active ingredient, preferably from about 25% to about 70%.

Oral and nasal administration to the lungs can also be effected by aerosol delivery forms. For aerosol administration, the active ingredient is preferably supplied in finely divided form along with a surfactant and a propellant. Typical percentages of active ingredients are from about 0.01 to about 20% by weight, preferably from about 0.04 to about 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the tradename SPANS®) and the polyoxyethylene and polyoxypropylene derivatives of these esters. Mixed esters, such as mixed or natural glycerides may be employed. The preferred surface-active agents are the oleates or sorbitan, e.g., those sold under the tradenames ARLACEL® C (Sorbitan sesquioleate), SPAN® 80 (sorbitan monooleate) and SPAN® 85 (sorbitan trioleate). The surfactant may constitute from about 0.1% to about 20% by weight of the composition, preferably from about 0.25% to about 5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the tradename FREON®. Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

For topical administration, these compositions comprise an effective amount of a compound of this class in admixture with a pharmaceutically acceptable non-toxic carrier. A suitable range of composition would be from about 0.1% to about 10% active ingredient, and the balance carrier, preferably from about 1% to about 2% active ingredient. The concentration of active ingredient in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of compounds of the present invention contains about 15 to about 45 percent of a saturated fatty alcohol having 16 to 24 carbon atoms such as cetyl alcohol, stearyl alcohol, behenyl alcohol, and the like and about 45 to about 85 wt. percent of a glycol solvent such as propylene glycol, polyethylene glycol, dipropylene glycol, and mixtures thereof. The ointment can also contain from about 0 to about 15 wt. percent of a plasticizer such as polyethylene glycol, 1,2,6-hexanetriol, sorbitol, glycerol, and the like; from about 0 to about 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding mono-ester of other fatty acids such as oleic acid and palmitic acid; and from about 0 to about 20 wt. percent of a penetrant such as dimethyl sulfoxide or dimethylacetamide.

A therapeutically active amount of the crystalline monosodium salt of D-isoglutamyl-D-tryptophan may vary according to factors such as disease state, age, sex, and weight of the individual. Dosage regime may be altered to provide the optimum therapeutic response. Generally, the daily regimen should be in the range of from about 1 to about 200 mg of peptide.

The following are examples of representative formulations and in no way restrict the scope of in the preparation of different pharmaceutical compositions.

| Ingredients | Quantity per tablet mgs |
|---|---|
| Active ingredient | 25 |
| lactose, spray-dried | 20 |
| Corn starch | 153 |
| magnesium stearate | 2 |

The above ingredients are thoroughly mixed and pressed into single scored tablets.

| Ingredients | Quantity per tablet mgs |
|---|---|
| Active ingredient | 100 |
| lactose, spray-dried | 148 |
| magnesium stearate | 2 |

The above ingredients are mixed and introduced into a hard-shell gelatin capsule.

| Ingredients | Quantity per tablet mgs |
|---|---|
| Active ingredient | 200 |
| lactose | 145 |
| cornstarch | 50 |
| magnesium stearate | 5 |

The above ingredients are mixed intimately and pressed into single scored tablets.

| Ingredients | Quantity per tablet mgs |
|---|---|
| Active ingredient | 108 |
| lactose | 15 |
| cornstarch | 25 |
| magnesium stearate | 2 |

The above ingredients are mixed and introduced into a hard-shell gelatin capsule.

| Ingredients | Quantity per tablet mgs |
|---|---|
| Active ingredient | 150 |
| lactose | 92 |

The above ingredients are mixed and introduced into a hard-shell gelatin capsule.

An injectable preparation buffered to a pH of 7 is prepared having the following composition:

| Ingredients | |
|---|---|
| Active ingredient | 0.2 g |

-continued

| Ingredients | |
|---|---|
| KH$_2$PO$_4$ | 2 ml |
| KOH (1N) | q.s. to pH 7 |
| Water (distilled, sterile) | q.s. to 20 ml |

An injectable preparation buffered to a pH of 7 is prepared having the following composition:

| Ingredients | |
|---|---|
| Active ingredient | 0.01 g |
| Water (distilled, sterile) | q.s. to 1 ml |
| NaOH (0.2N) | q.s. to pH 7 |

An oral suspension is prepared having the following composition:

| Ingredients | |
|---|---|
| Active ingredient | 0.1 g |
| fumaric acid | 0.5 g |
| methyl paraben | 2.0 g |
| granulated sugar | 0.1 g |
| sorbitol (70% solution) | 25.5 g |
| Veegum K (Vanderbilt Co.) | 12.85 g |
| flavoring | 1.0 g |
| colorings | 0.035 ml |
| distilled water | q.s. to 100 ml |

Topical Formulation

| Ingredients | Grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| distilled water | q.s. 100 ml |

All of the above ingredients, except water, are combined and heated to 45 degree C. with stirring. A sufficient quantity of water at 45 degree C. is then added with vigorous stirring to emulsify the ingredients, and water then added q.s. 100 g.

Further details of the preferred embodiments of the present invention are illustrated in the following examples which are understood to be non-limiting with respect to the appended claims.

EXAMPLES

Example 1

Preparation of Crystal Modification 1 (Polymorphic Form F) of the Mono-sodium Salt of D-isoglutamyl-D-tryptophan (1:1)

Method A: From the Mono-ammonium Salt of D-isoglutamyl-D-tryptophan (1:1) and Sodium Hydroxide.

A solution of H-D-iGlu-D-Trp-OH, mono-ammonium salt (1:1), (496 mg, 1.34 mmol) and 1N sodium hydroxide (1.4 mL, 1.40 mmol) in water (15 mL) was stirred at room temperature for 30 min. The reaction mixture was evaporated under reduced pressure to about 1-2 mL of solvent. After cooling down to room temperature, isopropanol (30 mL) was added until a solid precipitated out. The resulting suspension was stirred overnight at room temperature, after which the solid was collected by suction filtration. The solid was washed with isopropanol (2×40 mL) and then dried overnight in an oven at 44° C. An off white crystalline solid was obtained (462 mg, 97% yield). This material is named crystal modification 1 (polymorphic form F) of the mono-sodium salt of D-isoglutamyl-D-tryptophan (1:1).

The water content of this material was 3.4% as determined by Karl-Fischer test.

MS (m/z): 356.0 [M]$^+$, 334.1 [C$_{16}$H$_{20}$N$_3$O$_5$]$^+$, 187.9 (100%).

Figure 2:
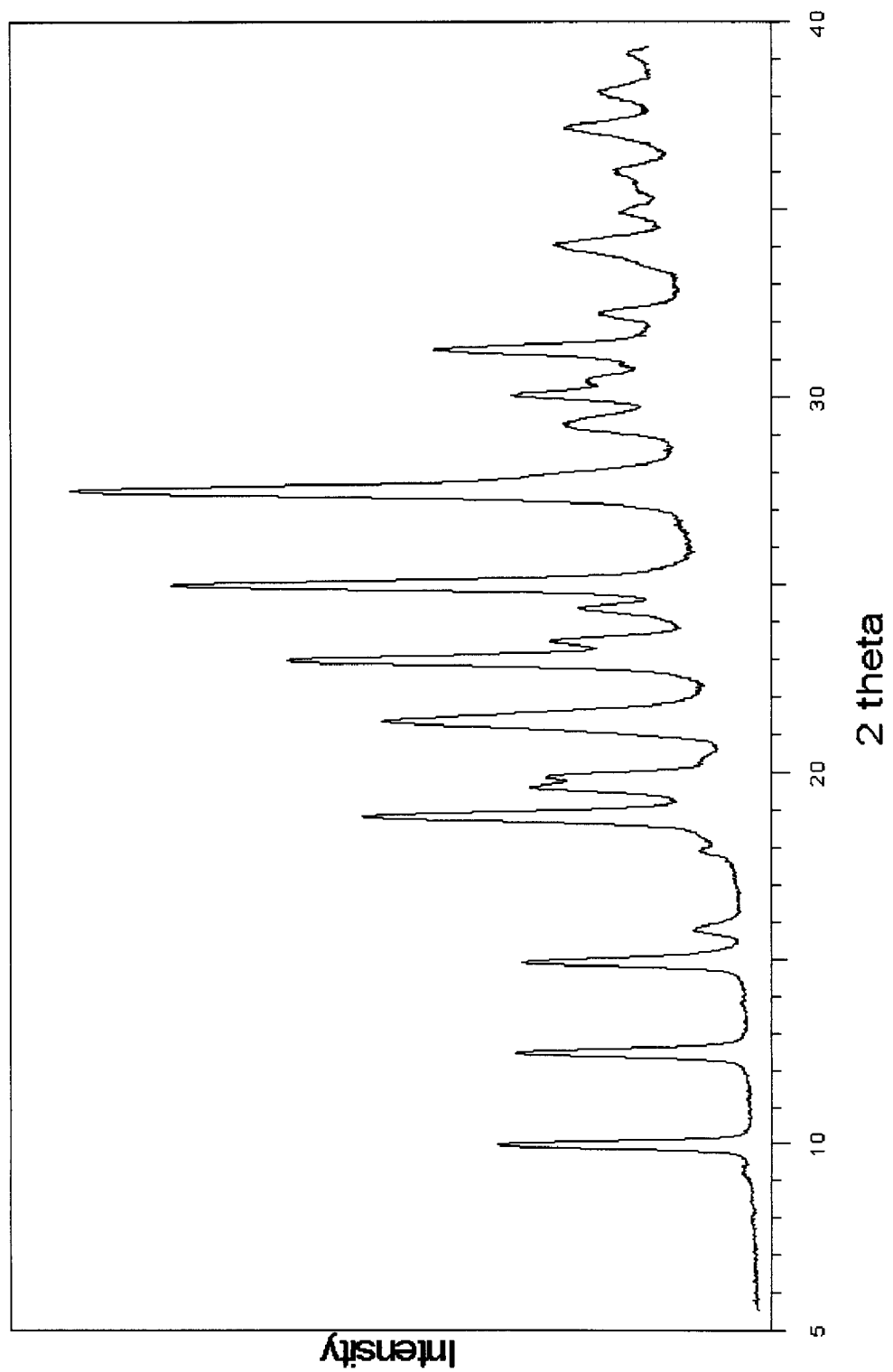
FIG. 2 is a characteristic XRPD pattern of crystal modification 1 (polymorphic form F) of the mono-sodium salt of D-isoglutamyl-D-tryptophan.

The XRPD pattern of this material is shown in FIG. 2. This XRPD pattern may also be expressed in terms of inter-planar distances d, Bragg's angle 2 theta, and relative intensity (expressed as a percentage with respect to the most intense ray) as follows:

| 2 Theta (°) | D-spacing (Angstrom) | Relative Intensity (%) |
|---|---|---|
| 9.23 | 9.573 | 2 |
| 9.91 | 8.917 | 41.3 |
| 12.41 | 7.126 | 37.6 |
| 13.76 | 6.43 | 0.8 |
| 14.87 | 5.954 | 35.8 |
| 15.75 | 5.622 | 7.6 |
| 17.88 | 4.957 | 5.5 |
| 18.78 | 4.721 | 58.9 |
| 19.57 | 4.532 | 30.9 |
| 19.84 | 4.471 | 28.1 |
| 20.31 | 4.368 | 2.9 |
| 21.32 | 4.165 | 53.5 |
| 21.55 | 4.12 | 30.3 |
| 22.95 | 3.873 | 67.4 |
| 23.45 | 3.79 | 24.5 |
| 24.34 | 3.654 | 19.4 |
| 24.96 | 3.565 | 85.2 |
| 27.49 | 3.242 | 100 |
| 27.94 | 3.19 | 23.3 |
| 29.27 | 3.049 | 19.1 |
| 30.07 | 2.97 | 27.2 |
| 30.43 | 2.935 | 15.2 |
| 31.29 | 2.856 | 39.9 |
| 32.25 | 2.774 | 13 |
| 34.07 | 2.629 | 19.3 |
| 34.94 | 2.566 | 7.8 |
| 35.53 | 2.525 | 5 |
| 36.08 | 2.487 | 8.4 |
| 37.21 | 2.414 | 15.5 |
| 38.17 | 2.356 | 9.1 |

The powdered samples were prepared by a normal front packing technique and run on a D8 Discovery Diffractometer system with Cu-kα source operating at 45 kV/45 mA. The system is equipped with 2D-proportional area detector (GADDS). The experimental data were collected on two frames at 600 s exposure of each one that covered the range of 3°-35° (2-theta). The obtained 2D diffraction images were then integrated in order to obtain standard, I vs. 2-theta, diffraction patterns. The data were processed by various Bruker AXS data processing software including: EVA™ 8.0 and TOPAS™ v. 2.1 (for profile fitting analysis and applications, when necessary). All of the XRPD patterns included herein were determined using the technique, instrument and settings as described above.

Figure 5:
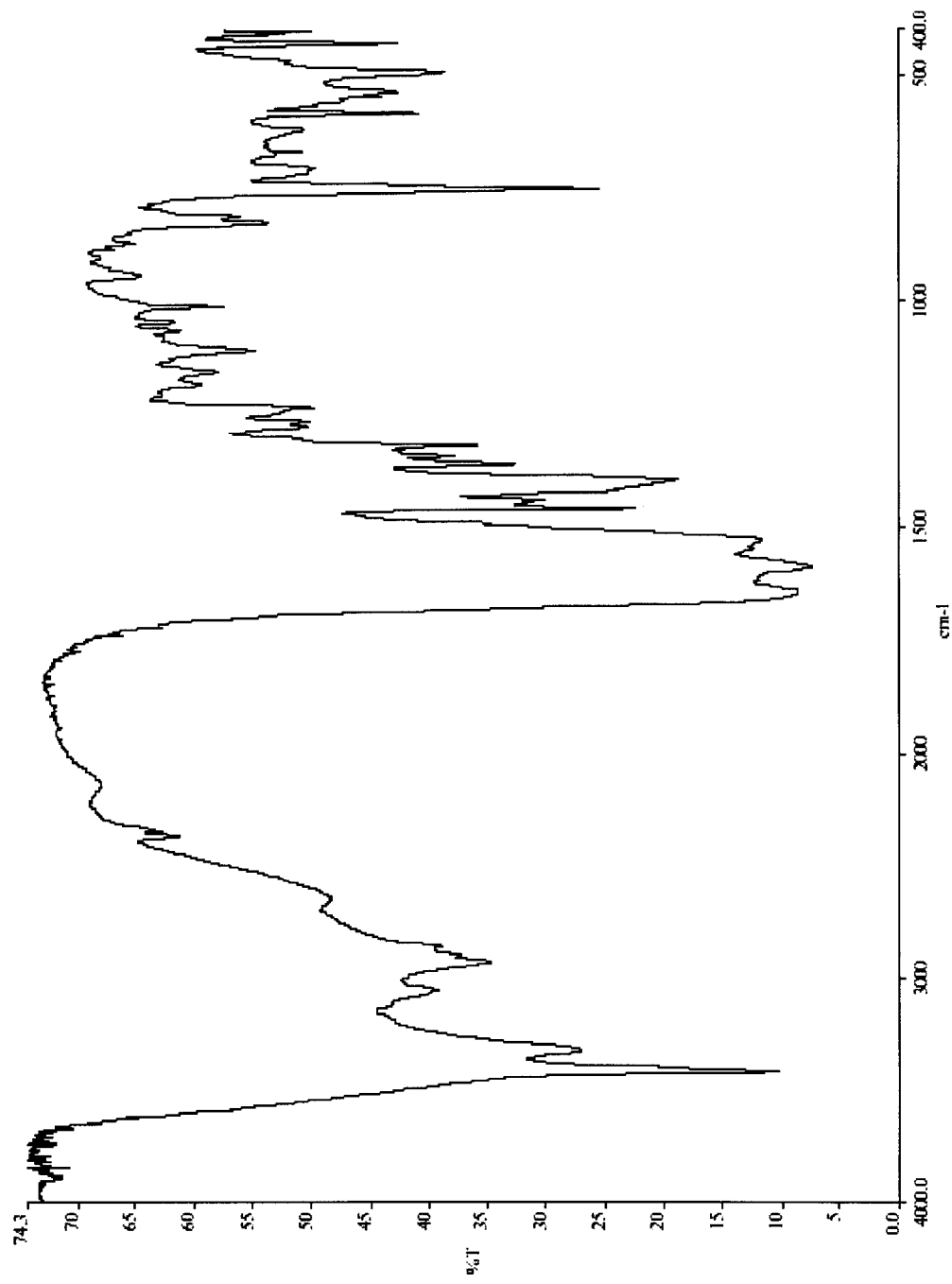
FIG. 5 is a characteristic infrared (IR) absorption spectrum of crystal modification 1 (polymorphic form F) of the mono-sodium salt of D-isoglutamyl-D-tryptophan.

The FT-IR (KBr) spectrum of this material is shown in FIG. 5.

Method B: From D-isoglutamyl-D-tryptophan and Sodium Hydroxide.

In a 100 mL round bottom flask equipped with a magnetic stir bar was placed 2.91 mL of sodium hydroxide (1.000 N, 2.91 mmol.) and 2.91 mL of deionized water. The solution was cooled to 0° C. using an ice water bath, and solid H-D-iGlu-D-Trp-OH (1.00 g, 3.00 mmol) was added all at once. Another 3 mL of deionized water was added, and the resulting solution was stirred for another 15 min. The pH of the solution was about 5.5 to about 6.0. The pH was adjusted to about 6.5 with the addition of 40 µM of a 0.500N solution of NaOH solution. The mixture was filtered to remove any solid particulates, and the filtrate was then concentrated in vacuo to about 0.5 mL of solution at a bath temperature of 30° C. The residue was diluted with 0.6 mL of deionized water and isopropanol (10 mL) was added with vigorous stirring and a solid precipitated out. The mixture was sonicated for a few min. Then, another 30 mL of isopropanol was added. After stirring for 90 min, the mixture was divided into two parts (A and B).

A. The Part A mixture was filtered and the solid was washed with isopropanol (2×10 mL). The solid was air dried for about 1 h, and then dried overnight under vacuum in an oven at 40° C. The XRPD pattern and IR (KBr) spectrum of this part A material are similar to the polymorphic form F shown in FIG. 2 and FIG. 5, respectively as described in Method A above.

B. The Part B mixture was stirred overnight. The mixture was then filtered, and the solid was washed with 2×10 mL of isopropanol, air dried for about 15 min, then dried overnight under vacuum at 40° C. The XRPD pattern and IR (KBr) spectrum of this part B material are similar to the polymorphic form F shown in FIG. 2 and FIG. 5, respectively as described in Method A above.

Example 2

Preparation of Crystal Modification 2 (Polymorphic Form I) of the Mono-sodium Salt of D-isoglutamyl-D-tryptophan (1:1)

In a 100 mL round bottom flask equipped with a magnetic stir bar was placed 2.97 mL of sodium hydroxide (1.000 N, 2.97 mmol.) and 3.0 mL of deionized water. The solution was cooled to 0° C. using an ice water bath, and solid H-D-iGlu-D-Trp-OH (1.00 g, 3.00 mmol) was added all at once, to give a clear slightly pinkish solution. The pH of the solution was about 7.0. The mixture was filtered to remove any solid particulates, and the filtrate was then concentrated in vacuo to give an oil. The residue was diluted with 0.6 mL of deionized water, and isopropanol (40 mL) was added with vigorous stirring and a solid precipitated out. After stirring for 1 h, the mixture was then filtered, and the solid was washed with 2×15 mL of isopropanol, air dried for about 15 min, then dried overnight under vacuum at 36° C. A white crystalline solid was obtained (1.00 g, 94% yield). This material is named crystal modification 2 (polymorphic form I) of the mono-sodium salt of D-isoglutamyl-D-tryptophan (1:1).

This material had an HPLC purity (peak area percent) of 98.5%. HPLC method; Column: XTerra MS C18; 5 µm, 4.6× 250 mm; Mobile phase: A=the aqueous phase: 4 mM Tris, 2 mM EDTA, pH 7.4; B=the organic phase: $CH_3CN$; gradient: B %: 0 min. 5%, 15 min. 55%, 30 min. 55%, 32 min. 5%, 35 min. 5%; Flow rate: 1 mL/min; injection volume: 5 µL; λ: 222, 254, 280, 450 nm; retention time of the product: 6.39 min.

The water content of this material was 6.0% as determined by Karl-Fischer test.

UV (water, c=22.4 µM, $\lambda_{max}$ nm): 221 (ε 30528), 280 (ε 4958).

MS (m/z): 356.0 $[M]^+$, 334.2 $[C_{16}H_{20}N_3O_5]^+$, 187.9 (100%).

Figure 3:
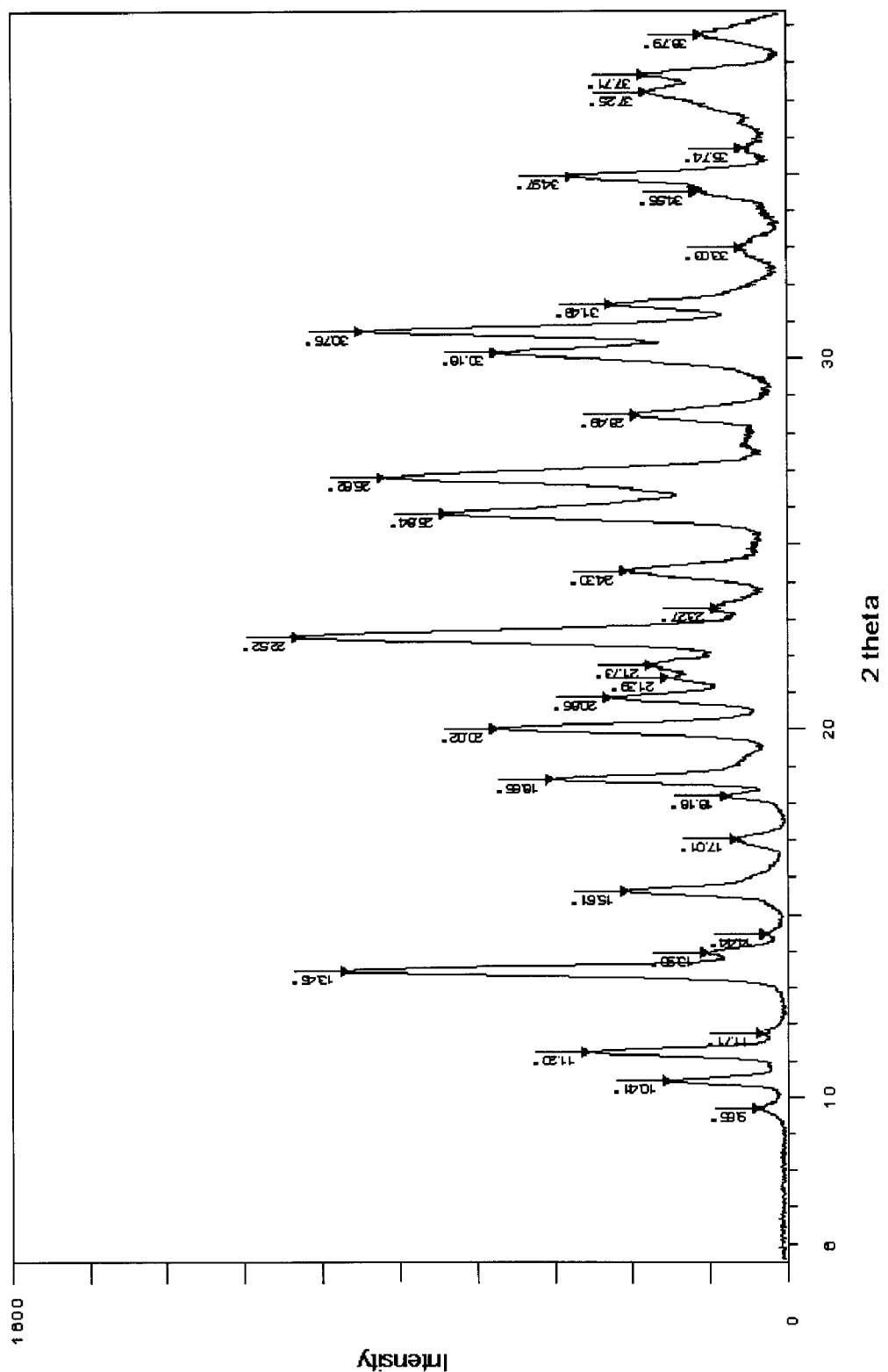
FIG. 3 is a characteristic XRPD pattern of crystal modification 2 (polymorphic form I) of the mono-sodium salt of D-isoglutamyl-D-tryptophan.

The XRPD pattern of this material is shown in FIG. 3. The XRPD pattern may also be expressed in terms of inter-planar distances d, Bragg's angle 2 theta, and relative intensity (expressed as a percentage with respect to the most intense ray) as follows:

| 2 Theta (°) | D-spacing (Angstrom) | Relative Intensity (%) |
|---|---|---|
| 9.65 | 9.161 | 5.3 |
| 10.41 | 8.492 | 23.7 |
| 11.2 | 7.897 | 40.4 |
| 11.71 | 7.549 | 4.5 |
| 13.45 | 6.58 | 90.2 |
| 13.93 | 6.351 | 15.9 |
| 14.44 | 6.128 | 3.7 |
| 15.61 | 5.672 | 32.4 |
| 17.01 | 5.207 | 9.9 |
| 18.18 | 4.876 | 11.7 |
| 18.65 | 4.755 | 47.8 |
| 20.02 | 4.432 | 59.2 |
| 20.85 | 4.257 | 35.9 |
| 21.39 | 4.15 | 24.1 |
| 21.73 | 4.086 | 27.3 |
| 22.52 | 3.945 | 100 |
| 23.27 | 3.819 | 13.7 |
| 24.3 | 3.66 | 32.4 |
| 25.84 | 3.445 | 69.5 |
| 26.82 | 3.322 | 82.5 |
| 28.49 | 3.13 | 30.1 |
| 30.18 | 2.959 | 58.8 |
| 30.76 | 2.904 | 86.9 |
| 31.49 | 2.839 | 35.3 |
| 33.03 | 2.71 | 8.7 |
| 34.55 | 2.594 | 17.8 |
| 34.97 | 2.564 | 43.4 |
| 35.74 | 2.51 | 8.5 |
| 37.25 | 2.412 | 28.1 |
| 37.71 | 2.383 | 28.5 |
| 38.79 | 2.319 | 16.9 |

Figure 6:
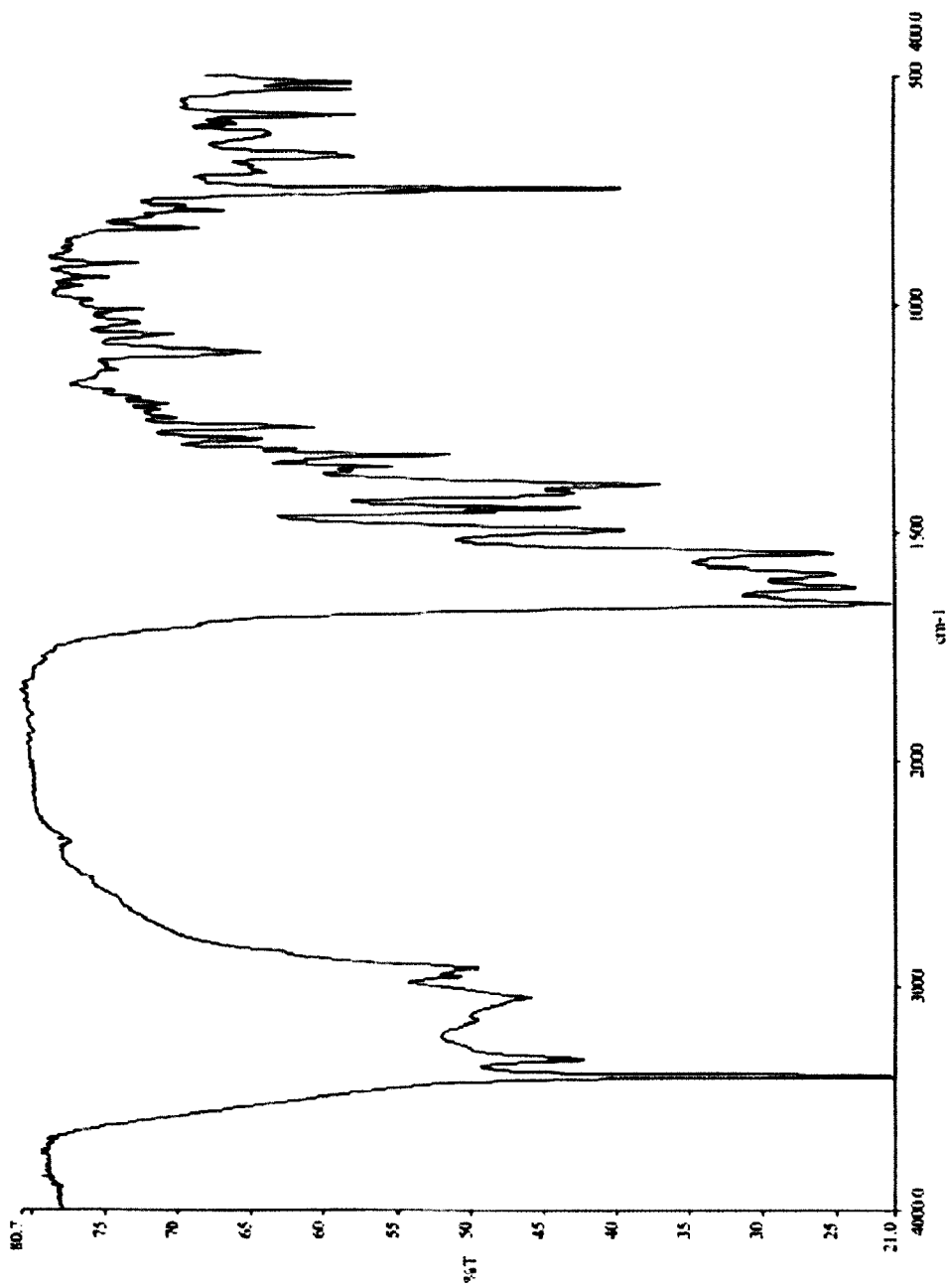
FIG. 6 is a characteristic infrared (IR) absorption spectrum of crystal modification 2 (polymorphic form I) of the mono-sodium salt of D-isoglutamyl-D-tryptophan.

The FT-IR (KBr) spectrum of this material is shown in FIG. 6.

This material was prepared in a similar manner as described below:

De-ionized water (18 mL) and 1N NaOH solution (18.0 mL, 18 mmol) were combined in a 250 mL round bottom flask and cooled to 0° C. Solid H-D-iGlu-D-Trp-OH (6.0 g, 18 mmol) was added and slowly dissolved. After 1 h, the solution had become a pale peach colour. A portion of this solution (6 mL) was removed and evaporated in vacuo to an oil. The oil was diluted with 0.6 mL of de-ionized water and IPA (40 mL) was added dropwise. The mixture was stirred vigorously for 1 h and then filtered. The solid was air dried and then dried overnight in a vacuum oven to afford 450 mg of the compound as a white solid, mp: 186.9-189.2° C. The XRPD and IR spectra of this material were similar to those provided in FIG. 3 and FIG. 6, respectively as described above.

Example 3

Preparation of Crystal Modification 3 (polymorphic form X) of the Mono-sodium Salt of D-isoglutamyl-D-tryptophan (1:1)

Method A: Solid mono-sodium salt of D-isoglutamyl-D-tryptophan (800 mg) prepared as described in Example 1, Method B above, was suspended in methanol (10 mL). The mixture was slightly heated to dissolve the solid. The solution was filtered twice through a sintered glass funnel and collected into a 100 mL round bottom flask. The flask was equipped with a stir bar and IPA (4 mL) was added slowly until a solid formed. The suspension was stirred for 4 h and then filtered. The solid was washed with IPA (3×10 mL). The solid was air-dried (solid became a pale peach colour) and then dried overnight in a vacuum oven. A white crystalline solid was obtained (480 mg, 60% yield), mp: 182.3-186.1° C. This material is named crystal modification 3 (polymorphic form X) of the mono-sodium salt of D-isoglutamyl-D-tryptophan (1:1).

Figure 4:
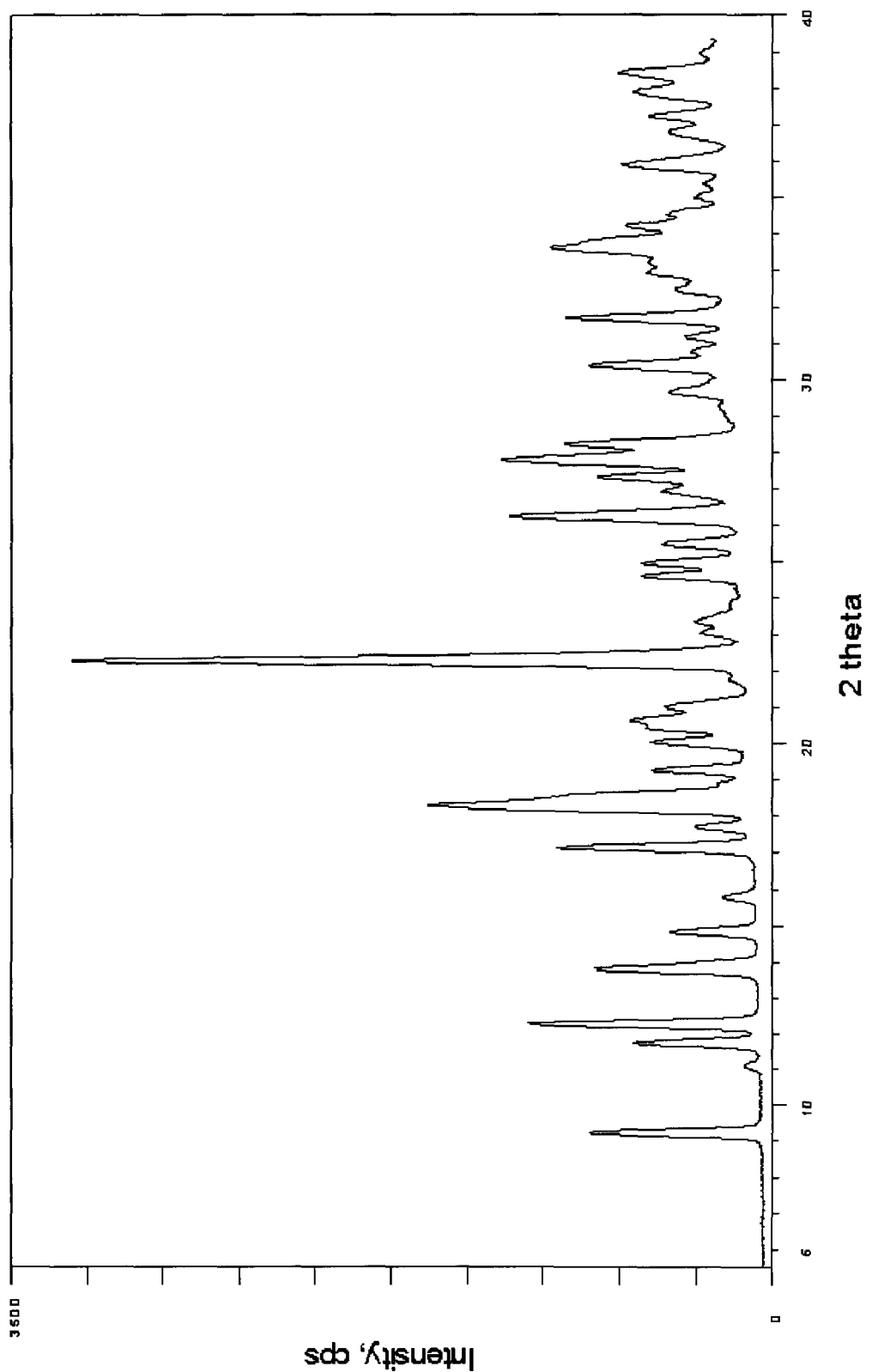
FIG. 4 is a characteristic XRPD pattern of crystal modification 3 (polymorphic form X) of the mono-sodium salt of D-isoglutamyl-D-tryptophan.

The XRPD pattern of this material is shown in FIG. 4. The XRPD pattern may also be expressed in terms of inter-planar distances d, Bragg's angle 2 theta, and relative intensity (expressed as a percentage with respect to the most intense ray) as follows:

| 2 Theta (°) | D-spacing (Angstrom) | Relative Intensity (%) |
|---|---|---|
| 9.187 | 9.618 | 25.4 |
| 11.058 | 7.995 | 2.3 |
| 11.713 | 7.549 | 18.7 |
| 12.239 | 7.226 | 34.2 |
| 13.785 | 6.419 | 23.5 |
| 14.806 | 5.978 | 13 |
| 15.763 | 5.618 | 5 |
| 17.126 | 5.173 | 29.3 |
| 17.693 | 5.009 | 8.4 |
| 18.268 | 4.852 | 48.2 |
| 18.562 | 4.776 | 28.2 |
| 19.261 | 4.604 | 14.3 |
| 20.033 | 4.429 | 14.5 |
| 20.63 | 4.302 | 17.2 |
| 21.006 | 4.226 | 12 |
| 21.778 | 4.078 | 2.4 |
| 22.268 | 3.989 | 100 |
| 23.054 | 3.855 | 6.4 |
| 23.361 | 3.805 | 7.4 |
| 23.851 | 3.728 | 1.8 |
| 24.626 | 3.612 | 14.9 |
| 24.981 | 3.562 | 14.7 |
| 25.507 | 3.489 | 11.1 |
| 26.257 | 3.391 | 34.3 |
| 26.963 | 3.304 | 11.1 |
| 27.329 | 3.261 | 20.6 |
| 27.807 | 3.206 | 35 |
| 28.243 | 3.157 | 25.6 |
| 28.975 | 3.079 | 1.1 |
| 29.264 | 3.049 | 2.3 |
| 29.687 | 3.007 | 9.5 |
| 30.409 | 2.937 | 20.9 |
| 30.798 | 2.901 | 6.1 |
| 31.193 | 2.865 | 6.9 |
| 31.724 | 2.818 | 24.7 |
| 32.505 | 2.752 | 8 |
| 32.985 | 2.713 | 12.1 |
| 33.645 | 2.662 | 26.5 |
| 34.249 | 2.616 | 15.2 |
| 34.587 | 2.591 | 8.6 |
| 35.048 | 2.558 | 4.6 |
| 35.41 | 2.533 | 3.3 |
| 35.933 | 2.497 | 15.3 |
| 36.833 | 2.438 | 8 |
| 37.276 | 2.41 | 10.8 |
| 37.937 | 2.37 | 12.7 |
| 38.467 | 2.338 | 14.7 |
| 39 | 2.308 | 2.6 |

The water content of this material was 9.3% as determined by Karl-Fischer test.

MS (m/z): 356.0 [M]$^+$, 334.2 [$C_{16}H_{20}N_3O_5$]$^+$, 187.9 (100%).

Figure 7:
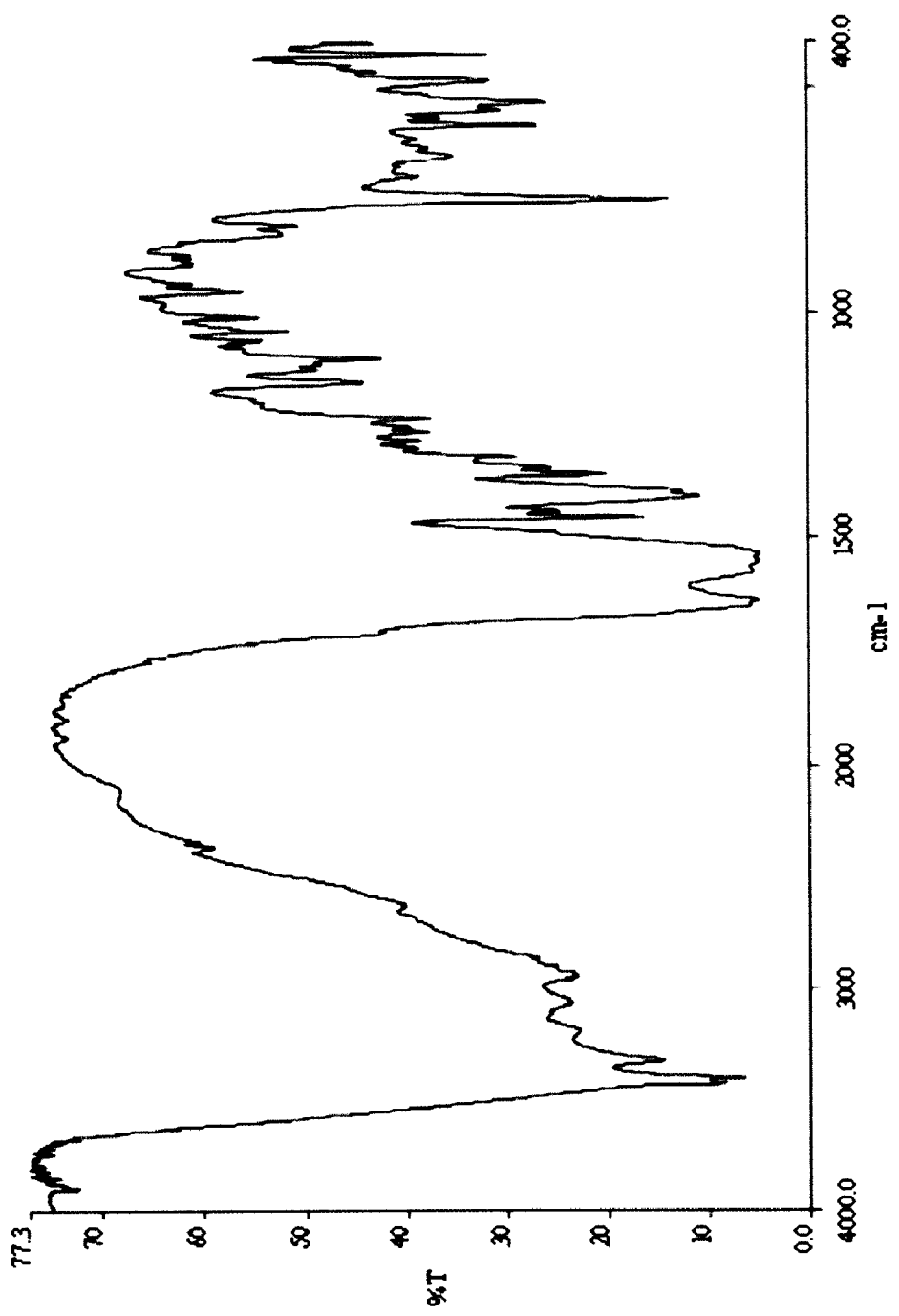
FIG. 7 is a characteristic infrared (IR) absorption spectrum of crystal modification 3 (polymorphic form X) of the mono-sodium salt of D-isoglutamyl-D-tryptophan.
Figure 8:
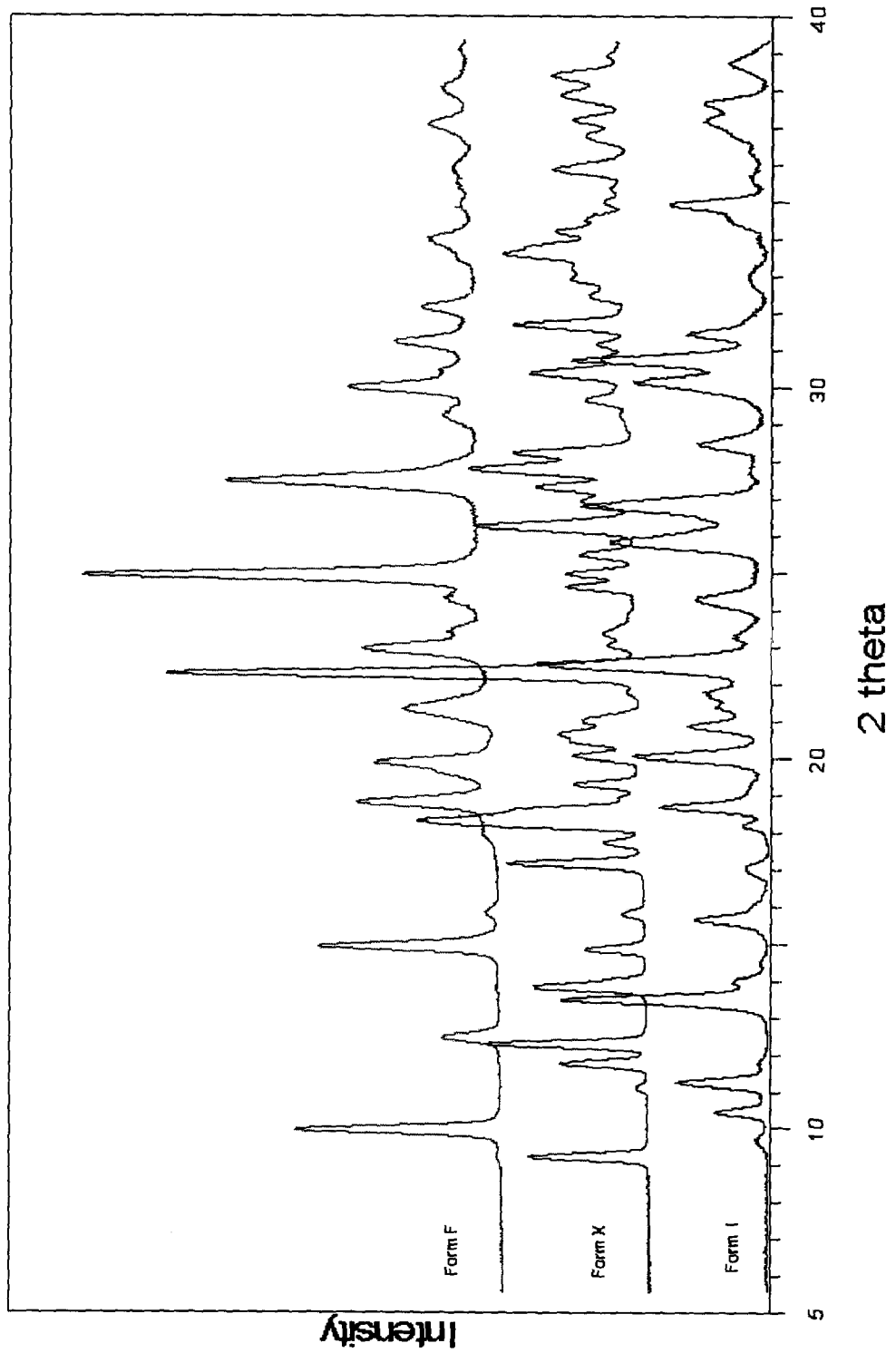
FIG. 8 shows the comparison of the XRPD pattern of crystal modification 1 (polymorphic form F), crystal modification 2 (polymorphic form I), and crystal modification 3 (polymorphic form X) of the mono-sodium salt of D-isoglutamyl-D-tryptophan.

The FT-IR (KBr) spectrum is provided in FIG. 7.

Method B: De-ionized water (6 mL) and 1N NaOH solution (6.0 mL, 6 mmol) were mixed in a 100 mL round bottom flask and cooled to 0° C. Solid H-D-iGlu-D-Trp-OH (2.0 g, 6 mmol) was added, and the mixture was sonicated for about 2 min to dissolve all of the solid. The pH of the solution was about 6.0. A portion of this solution (6 mL) was removed and filtered to remove any solid particulates. The filtrate was evaporated in vacuo to give a solid (1.02 g). A portion of the solid (0.5 g) was dissolved in de-ionized water (10 mL) to give a clear colorless solution. Volatiles were removed in vacuo using a rotary evaporator with ice-water for condenser cooling and at a bath temperature of 30° C. over a period of 6 h to give a solid. The XRPD pattern and IR spectrum of this material were similar to those provided in FIG. 4 and FIG. 7, respectively as described in Method A above.

Example 4

Preparation of Mixture of Crystal Modification 1 (Polymorphic Form F) and Crystal Modification 3 (Polymorphic Form X) of the Mono-sodium Salt of D-isoglutamyl-D-tryptophan (1:1)

In a 50 mL round bottom flask equipped with a magnetic stir bar was placed 3.0 mL of NaOH (1.0 M, 3 mmol) and 3 mL of distilled water. The solution was cooled to 0° C. using an ice water bath, and solid H-D-iGlu-D-Trp-OH (1.00 g, 3.0 mmol) was added to give a clear pink solution. The solution was allowed to stir at ice-cold temperature for 1 h and then warm to room temperature. The solution was filtered and then concentrated to about 1 mL of solvent. IPA (38 mL) was added until a solid precipitate formed. The solution was stirred vigorously for 1 h. Half of this solution was filtered and washed with 2×15 mL of IPA. The solid was air dried, and then dried overnight in a vacuum oven at 35° C. to yield 379 mg of a white crystalline solid. This material is a mixture of crystal modification 1 (polymorphic form F) and crystal modification 3 (polymorphic form X) of the sodium salt of D-isoglutamyl-D-tryptophan (1:1). The XRPD pattern of this material is provided in FIG. 9.

A portion of the solid obtained as described above (50 mg) was suspended and stirred in 3 mL of ethyl acetate at room temperature. After 2.5 h, the solution was filtered, the solid was air-dried and then dried overnight in a vacuum oven to afford 38 mg (78% yield) of a white crystalline solid. Analysis of the XRPD pattern indicated that this material is essentially crystal modification 1 (polymorphic form F) of the mono-sodium salt of D-isoglutamyl-D-tryptophan (1:1) as described in Example 1 above, the XRPD pattern of which is provided in FIG. 2.

The XRPD patterns for crystal modifications 1, 2, and 3 of the mono-sodium salt of D-isoglutamyl-D-tryptophan described above are provided in FIGS. 2, 3 and 4, respectively. It will be understood by those skilled in the art that the 2-theta values in the XRPD patterns for crystal modifications 1, 2, and 3 of the mono-sodium salt of D-isoglutamyl-D-tryptophan may vary slightly from one machine to another and/or from one sample to another, and so the values quoted are not to be construed as absolute. 2-theta values should typically be reproducible to about ±0.2 degrees, preferably to about ±0.1 degrees. It will also be understood by those skilled in the art that the relative intensities of the peaks in the XRPD patterns for crystal modifications 1, 2 and 3 of the mono-sodium salt of D-isoglutamyl-D-tryptophan may vary considerably from one machine to another and/or from one sample to another, and so the values quoted are not to be construed as absolute.

Although preferred embodiments of the present invention have been described herein, it will be understood by those skilled in the art that variations may be made thereto without departing from the spirit of the invention or the scope of the appended claims.

The invention claimed is:

1. A crystalline mono-sodium salt of D-isoglutamyl-D-tryptophan, wherein the crystalline material is crystal modification 3 (polymorphic form X).

2. The crystal modification 3 (polymorphic form X) of the mono sodium salt of D-isoglutamyl-D-tryptophan of claim 1 having an XRPD pattern as shown in FIG. 4.

3. The crystal modification 3 (polymorphic form X) of the mono sodium salt of D-isoglutamyl-D-tryptophan of claim 1, having an XRPD pattern comprising peaks, in terms of 2-theta, at: 9.187±0.200, 11.058±0.200, 11.713±0.200, 12.239±0.200, 13.785±0.200, 14.806±0.200, 15.763±0.200, 17.126±0.200, 17.693±0.200, 18.268±0.200, 18.562±0.200, 19.261±0.200, 20.033±0.200, 20.63±0.200, 21.006±0.200, 21.778±0.200, 22.268±0.200, 23.054±0.200, 23.361±0.200, 23.851±0.200, 24.626±0.200, 24.981±0.200, 25.507±0.200, 26.257±0.200, 26.963±0.200, 27.329±0.200, 27.807±0.200, 28.243±0.200, 28.975±0.200, 29.264±0.200, 29.687±0.200, 30.409±0.200, 30.798±0.200, 31.193±0.200, 31.724±0.200, 32.505±0.200, 32.985±0.200, 33.645±0.200, 34.249±0.200, 34.587±0.200, 35.048±0.200, 35.41±0.200, 35.933±0.200, 36.833±0.200, 37.276±0.200, 37.937±0.200, 38.467±0.200, and 39±0.200.

4. The crystal modification 3 (polymorphic form X) of the mono-sodium salt of D-isoglutamyl-D-tryptophan of claim 1, having an XRPD pattern comprising peaks, in terms of 2-theta, at: 9.187±0.100, 11.058±0.100, 11.713±0.100, 12.239±0.100, 13.785±0.100, 14.806±0.100, 15.763±0.100, 17.126±0.100, 17.693±0.100, 18.268±0.100, 18.562±0.100, 19.261±0.100, 20.033±0.100, 20.63±0.100, 21.006±0.100, 21.778±0.100, 22.268±0.100, 23.054±0.100, 23.361±0.100, 23.851±0.100, 24.626±0.100, 24.981±0.100, 25.507±0.100, 26.257±0.100, 26.963±0.100, 27.329±0.100, 27.807±0.100, 28.243±0.100, 28.975±0.100, 29.264±0.100, 29.687±0.100, 30.409±0.100, 30.798±0.100, 31.193±0.100, 31.724±0.100, 32.505±0.100, 32.985±0.100, 33.645±0.100, 34.249±0.100, 34.587±0.100, 35.048±0.100, 35.41±0.100, 35.933±0.100, 36.833±0.100, 37.276±0.100, 37.937±0.100, 38.467±0.100, and 39±0.100.

5. The crystal modification 3 (polymorphic form X) of the mono sodium salt of D-isoglutamyl-D-tryptophan of claim 1, having an XRPD pattern measured using a diffractometer (copper anti-cathode) and expressed in terms of inter-planar distances d, Bragg's angle 2 theta, and relative intensity (expressed as a percentage with respect to the most intense ray) as follows:

| 2-Theta (°) | D-spacing (Angstrom) | Relative Intensity (%) |
|---|---|---|
| 9.187 | 9.618 | 25.4 |
| 11.058 | 7.995 | 2.3 |
| 11.713 | 7.549 | 18.7 |
| 12.239 | 7.226 | 34.2 |
| 13.785 | 6.419 | 23.5 |
| 14.806 | 5.978 | 13 |
| 15.763 | 5.618 | 5 |
| 17.126 | 5.173 | 29.3 |
| 17.693 | 5.009 | 8.4 |
| 18.268 | 4.852 | 48.2 |
| 18.562 | 4.776 | 28.2 |
| 19.261 | 4.604 | 14.3 |
| 20.033 | 4.429 | 14.5 |
| 20.630 | 4.302 | 17.2 |
| 21.006 | 4.226 | 12 |
| 21.778 | 4.078 | 2.4 |
| 22.268 | 3.989 | 100 |
| 23.054 | 3.855 | 6.4 |
| 23.361 | 3.805 | 7.4 |
| 23.851 | 3.728 | 1.8 |
| 24.626 | 3.612 | 14.9 |
| 24.981 | 3.562 | 14.7 |
| 25.507 | 3.489 | 11.1 |
| 26.257 | 3.391 | 34.3 |
| 26.963 | 3.304 | 11.1 |
| 27.329 | 3.261 | 20.6 |
| 27.807 | 3.206 | 35 |
| 28.243 | 3.157 | 25.6 |
| 28.975 | 3.079 | 1.1 |
| 29.264 | 3.049 | 2.3 |
| 29.687 | 3.007 | 9.5 |
| 30.409 | 2.937 | 20.9 |
| 30.798 | 2.901 | 6.1 |
| 31.193 | 2.865 | 6.9 |
| 31.724 | 2.818 | 24.7 |
| 32.505 | 2.752 | 8 |
| 32.985 | 2.713 | 12.1 |
| 33.645 | 2.662 | 26.5 |
| 34.249 | 2.616 | 15.2 |
| 34.587 | 2.591 | 8.6 |
| 35.048 | 2.558 | 4.6 |
| 35.410 | 2.533 | 3.3 |
| 35.933 | 2.497 | 15.3 |
| 36.833 | 2.438 | 8 |
| 37.276 | 2.41 | 10.8 |
| 37.937 | 2.37 | 12.7 |
| 38.467 | 2.338 | 14.7 |
| 39.000 | 2.308 | 2.6 |

6. A mixture comprising the crystalline mono-sodium salt of D-isoglutamyl-D-tryptophan of claim 1, and a crystal modification 1 (polymorphic form F) of the mono sodium salt of D-isoglutamyl-D-tryptophan.

Figure 9:
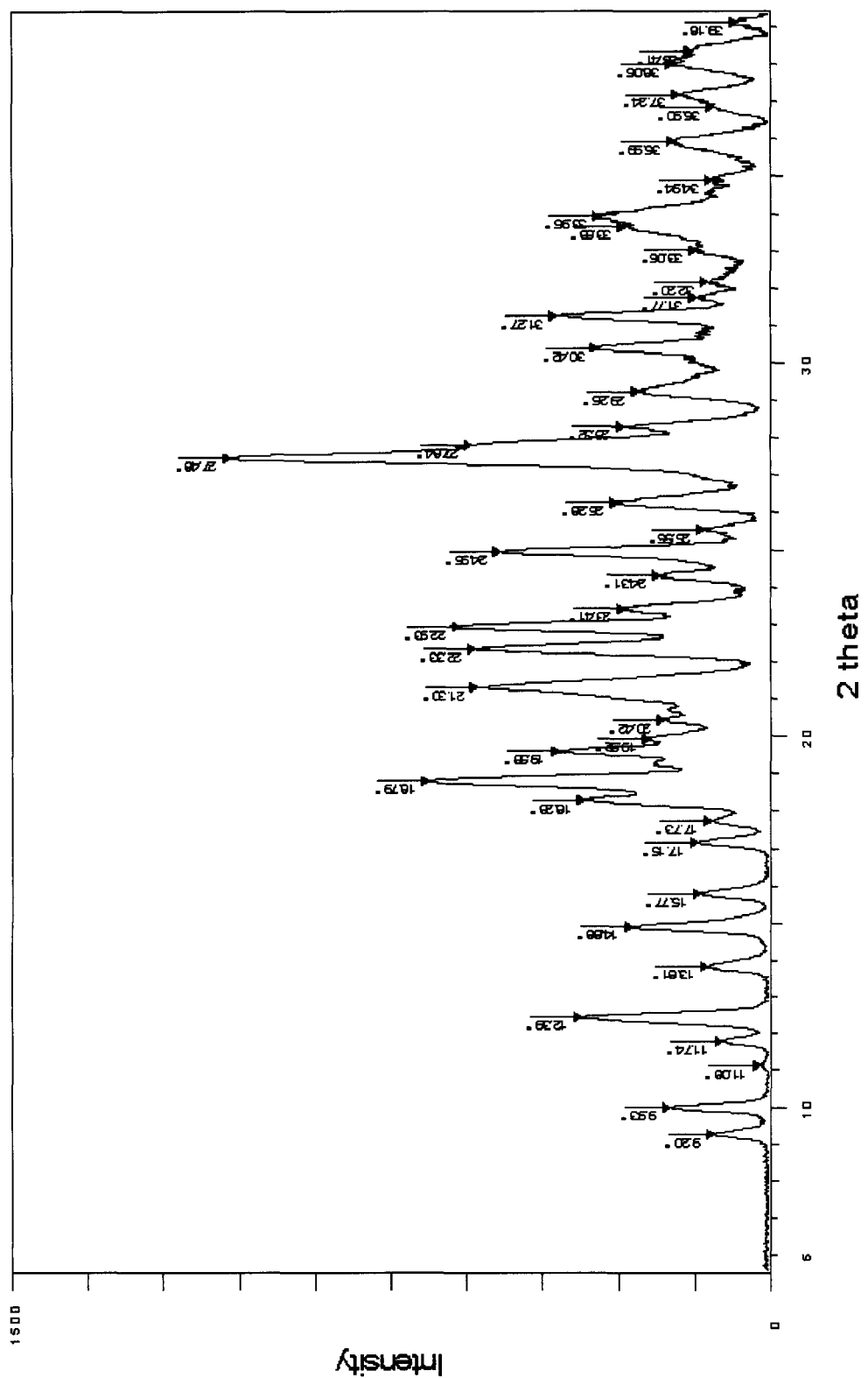
FIG. 9 is a characteristic XRPD pattern of a mixture of the crystal modification 1 (polymorphoric form F) and crystal modification 3 (polymorphic form X) of the mono-sodium salt of D-isoglutamyl-D-tryptophan.

7. The mixture of the crystal modification 1 (polymorphic form F) and the crystal modification 3 (polymorphic form X) of the mono sodium salt of D-isoglutamyl-D-tryptophan of claim 6 having an XRPD pattern as shown in FIG. 9.

8. The pharmaceutical composition comprising the crystalline mono-sodium salt of D-isoglutamyl-D-tryptophan is crystal modification 3 (polymorphic form X) of claim 1.

9. The pharmaceutical composition of claim 8 further comprising a mixture of crystal modification 1 (polymorphic form F) of the mono sodium salt of D-isoglutamyl-D-tryptophan.

* * * * *